United States Patent
Gallego Eckstein

(10) Patent No.: US 12,340,899 B1
(45) Date of Patent: Jun. 24, 2025

(54) APPARATUS, METHODS, AND SYSTEMS FOR REAL-TIME FEEDBACK IN MEDICAL PROCEDURES USING WEARABLE DEVICES WORN BY PROCEDURE PERFORMERS

(71) Applicant: Jeremy Gallego Eckstein, Miami, FL (US)

(72) Inventor: Jeremy Gallego Eckstein, Miami, FL (US)

( * ) Notice: Subject to any disclaimer, the term of this patent is extended or adjusted under 35 U.S.C. 154(b) by 0 days.

(21) Appl. No.: 18/744,430

(22) Filed: Jun. 14, 2024

(51) Int. Cl.
*G16H 40/20* (2018.01)

(52) U.S. Cl.
CPC .................................. *G16H 40/20* (2018.01)

(58) Field of Classification Search
CPC ....................................................... G16H 40/20
See application file for complete search history.

(56) References Cited

U.S. PATENT DOCUMENTS

| | | |
|---|---|---|
| 9,389,694 B2 | 7/2016 | Ataee et al. |
| 10,085,669 B2 | 10/2018 | Choi et al. |
| 10,199,008 B2 | 2/2019 | Aleem et al. |
| 10,466,783 B2 | 11/2019 | Newberry |
| 10,849,519 B2 | 12/2020 | Mendenhall et al. |
| 10,856,778 B2 | 12/2020 | Trigueiros Da Silva Cunha et al. |
| 11,850,420 B2 | 12/2023 | Aharonovitch et al. |
| 2009/0263775 A1* | 10/2009 | Ullrich .................. G09B 23/285 434/267 |

(Continued)

FOREIGN PATENT DOCUMENTS

| | | |
|---|---|---|
| EP | 3089726 B1 | 12/2021 |
| JP | 2023544609 A | 10/2023 |
| WO | WO2018081795 A1 | 5/2018 |

OTHER PUBLICATIONS

Helen Albert, "Hand-Movement Sensing Bracelet Could Revolutionize Activity Tracking", website: https://www.forbes.com/sites/helenalbert/2020/07/27/hnad-movement-sensor-could-revolutionize-activity-tracking/?sh=48a6dcd4f2e8.

(Continued)

*Primary Examiner* — Chinyere Mpamugo
(74) *Attorney, Agent, or Firm* — Derek Fahey, Esq.; The Plus IP Firm, PLLC

(57) ABSTRACT

A method for evaluating a user's performance of a medical procedure is disclosed. The method comprises receiving a plurality of training measured metrics collected from a sensor worn by the user during training medical procedures, where these metrics include physiological and biomechanical parameters. An algorithm is trained to identify types of medical procedures, procedural segments, and performance benchmarks. During the medical procedure, the sensor collects similar metrics, which are analyzed to identify the procedure type, procedural segments, and deviations from benchmarks. Feedback is provided based on these deviations. Additional steps include using a training model comprising a neural network with machine learning algorithms to analyze metrics, updating the training model with new data, initiating sensor calibration, detecting a predetermined movement pattern to start data collection, and identifying spatial reference points. The method further comprises providing real-time feedback to the user through haptic, auditory, and visual modalities based on performance deviations.

2 Claims, 24 Drawing Sheets

(56) References Cited

U.S. PATENT DOCUMENTS

| | | | |
|---|---|---|---|
| 2023/0181258 A1* | 6/2023 | Roh .................. | A61B 90/37 606/1 |
| 2023/0230498 A1* | 7/2023 | Fox .................. | G09B 19/003 |
| 2023/0290278 A1* | 9/2023 | Pugh ................. | G09B 19/003 |
| 2024/0161909 A1* | 5/2024 | Palma ................ | G16H 20/40 |

OTHER PUBLICATIONS

Vctor Horsley, "A Sensorised Surgical Glove to Analyze Forces During Neurosurgery", https://journals/www.com/neurosurgery/fulltext/2023/03000/a_sensorised_surgical_glove_to_analyze_forces24.aspx.

* cited by examiner

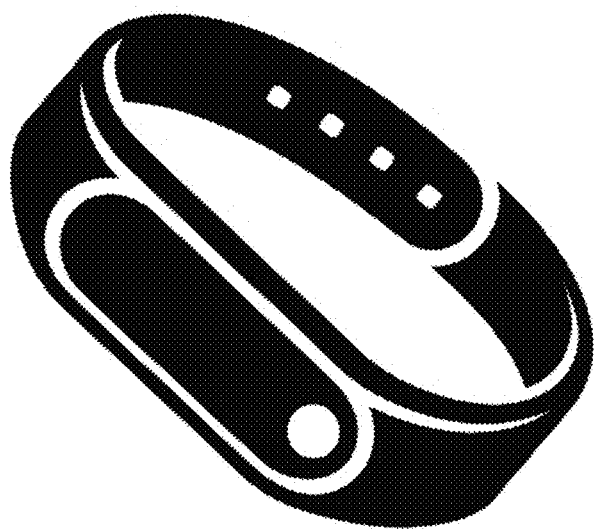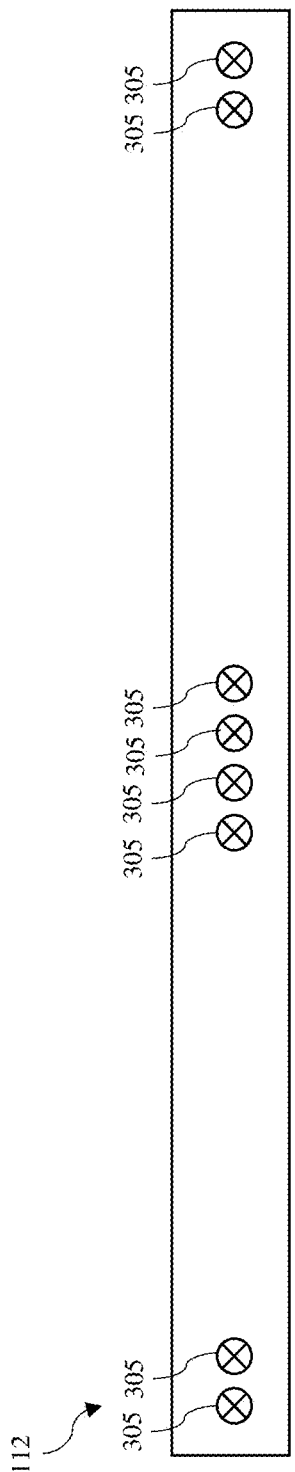
FIG. 3A
FIG. 3B

| Segment | X | Y | Z | SIGNAL 1 | SIGNAL 2 | SIGNAL 3 | SIGNAL 4 |
|---|---|---|---|---|---|---|---|
| 1-calibration | 0 | 0 | 0 | 0 | 0 | 0 | 0 |
| 2-request tool | -5 | 0 | -1 | 3 | 5 | 8 | 3 |
| 3-incision 1 | 3 | 4 | 7 | 5 | 7 | 9 | 3 |
| 4-incision 2 | 5 | 6 | 3 | 8 | 3 | 7 | 2 |
| 5-suture | 8 | 5 | 1 | 8 | 3 | 6 | 9 |
| 6-clean | 4 | 9 | 2 | 6 | 3 | 8 | 1 |

FIG. 11

Insertion of Ports ← 1528

1506 →

1548 →

| Deviations | |
|---|---|
| Active Time | -1 |
| Inactive Time | -1 |
| Instruments used | 2 |
| Forces | 4 |
| Total Deviation | 4 |

1530

1554 → *Suggested Score*: 92

1550 → Enter Segment Score

Laparoscopic Appendectomy ← 1507

1556 →

1558 →

| Deviations | |
|---|---|
| Active Time | -3 |
| Inactive Time | 3 |
| Operating Room Utilization | 0 |
| Instruments used | 2 |
| Forces | 8 |
| Total Deviation | 10 |

1564 → *Suggested Score*: 76

1560 → Enter Procedure Score

APPARATUS, METHODS, AND SYSTEMS FOR REAL-TIME FEEDBACK IN MEDICAL PROCEDURES USING WEARABLE DEVICES WORN BY PROCEDURE PERFORMERS

REFERENCE TO RELATED APPLICATIONS

Not applicable.

CROSS-REFERENCES

Not applicable.

STATEMENT REGARDING FEDERALLY SPONSORED RESEARCH OR DEVELOPMENT

Not applicable.

INCORPORATION BY REFERENCE OF MATERIAL SUBMITTED ON A COMPACT DISK

Not applicable.

TECHNICAL FIELD

The present disclosure relates to the field of healthcare technology, and more specifically to the field of wearable devices for medical procedures.

BACKGROUND OF THE INVENTION

The field of medical training and evaluation has undergone significant changes over the past few decades, primarily due to advancements in technology and a growing understanding of human physiology and biomechanics. Traditionally, medical training has relied heavily on direct observation, mentorship, and manual practice with feedback provided by experienced practitioners. However, this conventional approach often lacks quantifiable metrics, consistent benchmarks, and real-time, personalized feedback, which are crucial for objective assessment and improvement.

One of the persistent challenges in medical education is the variability in training quality across different institutions and geographies. This variability can lead to inconsistent competencies among medical professionals, potentially affecting patient outcomes. Furthermore, traditional training methods typically do not account for the individual physiological and biomechanical variations among trainees, which can significantly influence their performance and learning curves.

Additionally, with the increasing complexity of medical procedures and the rapid introduction of new technologies and techniques, there is a pressing need for more dynamic and adaptive training methods. These methods must not only accommodate varying skill levels and learning speeds but also integrate new medical knowledge and procedural updates effectively.

The development of wearable technology and sensor systems has provided opportunities to monitor and record detailed physiological and biomechanical data during medical procedures. However, effectively integrating this data into a cohesive training and evaluation system remains a challenge. Existing systems often do not fully exploit the potential of this data, lacking sophisticated algorithms capable of detailed analysis and real-time feedback mechanisms that could significantly enhance learning outcomes.

Thus, there exists a need for advanced systems that can utilize real-time data collection, incorporate machine learning to analyze and adapt to the trainee's performance, and provide immediate and actionable feedback across various sensory modalities. Such systems could improve medical training by making it more standardized, personalized, and responsive to the evolving landscape of medical practice.

BRIEF SUMMARY OF THE INVENTION

An apparatus, methods, and systems for evaluating a user's performance of a medical procedure are disclosed. This Summary is provided to introduce a selection of disclosed concepts in a simplified form that are further described below in the Detailed Description including the drawings provided. This Summary is not intended to identify key features or essential features of the claimed subject matter. Nor is this Summary intended to be used to limit the claimed subject matter's scope.

In one embodiment, a method for evaluating a user's performance of a medical procedure is disclosed. The method comprises receiving a plurality of training measured metrics collected from a sensor worn by the user while performing a plurality of training medical procedures. The plurality of training measured metrics comprises a physiological parameter and a biomechanical parameter measured during each of the plurality of training medical procedures. The method comprises training, based on the plurality of training measured metrics collected during the plurality of training medical procedures, an algorithm to identify a plurality of types of training medical procedures a plurality of procedural segments for each of the plurality of types of training medical procedures, and a performance benchmark for each of the plurality of types of training medical procedures. The method further comprises receiving, from the sensor worn by the user while performing the medical procedure, a plurality of measured metrics, wherein the plurality of measured metrics comprises the physiological parameter and the biomechanical parameter. The method comprises analyzing the plurality of measured metrics collected during the medical procedure so as to identify the medical procedure as one of the plurality of types, the plurality of procedural segments of the medical procedure; and a deviation between the performance benchmark and the plurality of measured metrics collected during the medical procedure. The method comprises displaying, on a display, the medical procedure as one of the plurality of types, the plurality of procedural segments of the medical procedure; and (iii) the deviation from the performance benchmark.

Said training comprises using a training model comprising a neural network in conjunction with at least one machine learning algorithm to analyze the plurality of training measured metrics collected during the plurality of training medical procedures to identify at least one type of medical procedure of the plurality of types of training medical procedures, at least one of the plurality of procedural segments, and the performance benchmark for the at least one type of medical procedure of the plurality of types of training medical procedures. The method further comprises updating the training model based on the plurality of measured metrics collected during the medical procedure.

Each of the plurality of procedural segments for each of the plurality of types of training medical procedures comprises a sub-benchmark of performance. The analyzing the plurality of measured metrics collected during the medical procedure further comprises applying the training model and comparing the plurality of measured metrics to the plurality of training measured metrics. The analyzing further includes identifying a first procedural segment for the medical procedure by comparing the plurality of measured metrics to the plurality of procedural segments of the training model. The analyzing further includes predicting a second procedural segment for the medical procedure based on the training model. The analyzing further includes calculating the deviation between the sub-benchmark of performance for the second procedural segment predicted by the training model and the plurality of measured metrics collected during the medical procedure. The analyzing further includes identifying the medical procedure as a first type of one of the plurality of types if the deviation is within a predetermined threshold.

The method further includes initiating a calibration process for the sensor prior to commencing the medical procedure. The method includes calibrating the sensor comprises detecting a predetermined movement pattern corresponding to a gesture to initiate the collecting of a plurality of sensor data. Said calibrating the sensor further comprises identifying at least one spatial reference point. The sensor collects a position of the sensor relative to the at least one spatial reference point and a state of a plurality of muscles of the user performing the medical procedure.

In some embodiments, the method includes providing real-time feedback to the user based on the deviation from the performance benchmark, wherein the feedback is selected from haptic, auditory, and visual feedback modalities.

Additional aspects of the disclosed embodiment will be set forth in part in the description which follows, and in part will be obvious from the description, or may be learned by practice of the disclosed embodiments. The aspects of the disclosed embodiments will be realized and attained by means of the elements and combinations particularly pointed out in the appended claims. It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute part of this specification, illustrate embodiments of the disclosure and together with the description, explain the principles of the disclosed embodiments. The embodiments illustrated herein are presently preferred, it being understood, however, that the disclosure is not limited to the precise arrangements and instrumentalities shown, wherein:

FIG. 3A is a perspective view of a wearable device, according to an example embodiment;

FIG. 3B is a bottom view of a wearable device, according to an example embodiment;

FIG. 11 is a table chart including data for a plurality of procedural segments, according to an example embodiment;

FIG. 15G illustrates a graphical user interface including calculated deviations for a procedural segment, according to an example embodiment;

FIG. 15H illustrates a graphical user interface including calculated deviations a procedural segment, according to an example embodiment;

Figure 1:
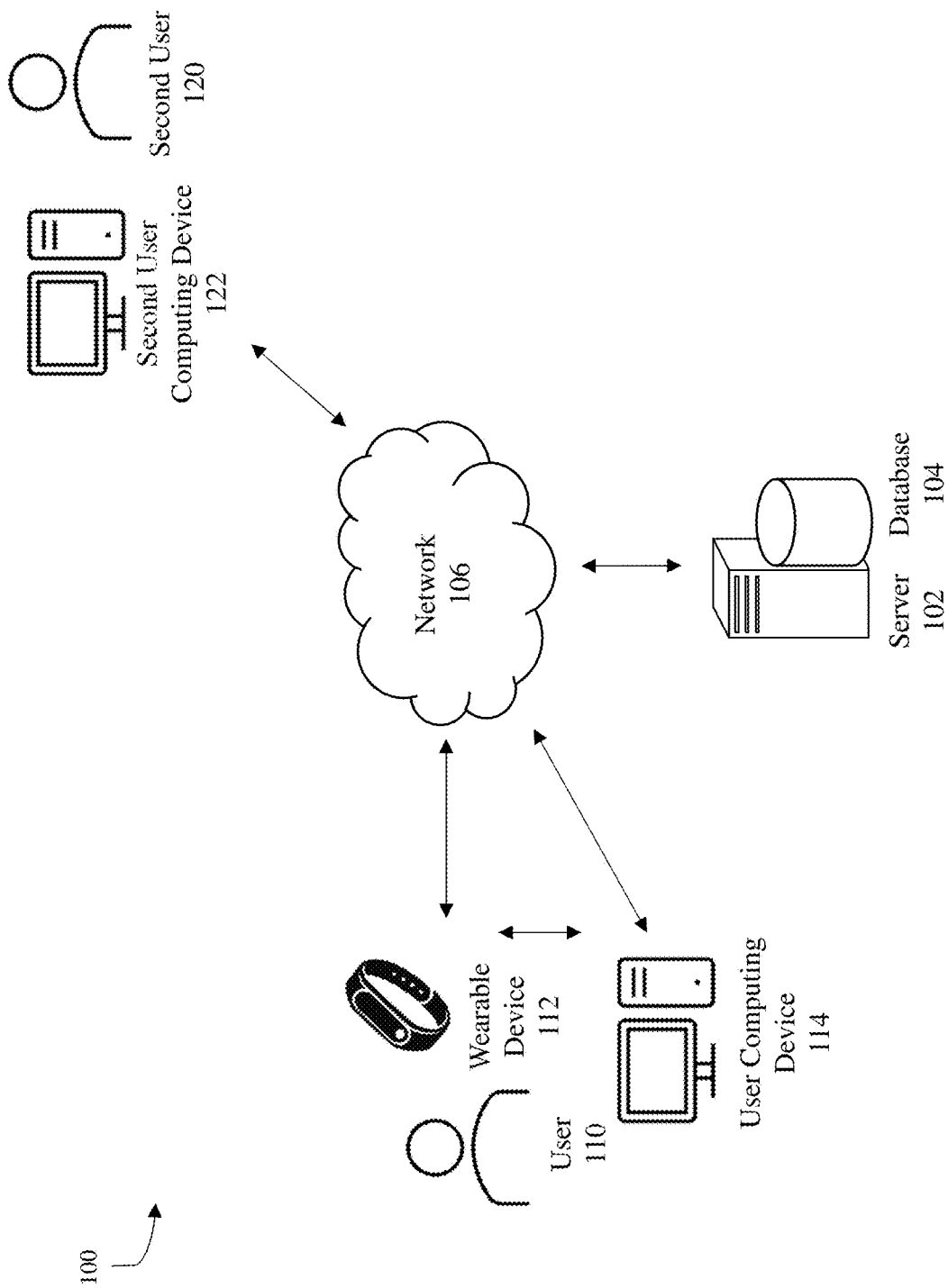
FIG. 1 is a diagram of an operating environment that supports a system for evaluating a user's performance of a medical procedure, according to an example embodiment.

Like reference numerals refer to like parts throughout the various views of the drawings. It should be noted that some aspects of the subject matter described herein are not easily illustrated, and the accompanying figures are provided as representative, non-limiting examples to aid in understanding the disclosure.

DETAILED DESCRIPTION

The following detailed description refers to the accompanying drawings. Whenever possible, the same reference numbers are used in the drawings and the following description to refer to the same or similar elements. While disclosed embodiments may be described, modifications, adaptations, and other implementations are possible. For example, substitutions, additions, or modifications may be made to the elements illustrated in the drawings, and the methods described herein may be modified by substituting reordering or adding additional stages or components to the disclosed methods and devices. Accordingly, the following detailed description does not limit the disclosed embodiments. Instead, the proper scope of the disclosed embodiments is defined by the appended claims.

Generally, the methods described herein are not limited to the particular order of the disclosed steps. While, in certain embodiments, the disclosed order may provide certain improvements over the prior art, it should be generally understood that the method steps may be rearranged, modified, or performed in alternative sequences without departing from the scope of the disclosure. In certain embodiments, the method steps may occur concurrently, simultaneously, independently, dependently, or in any other suitable manner, as determined by the specific implementation and requirements. The flexibility of the method allows for adaptability and optimization based on various factors, such as system resources, data availability, and user preferences. Therefore, the specific arrangement and order of the method steps should be interpreted as illustrative rather than limiting, and the disclosure encompasses all variations, modifications, and alternatives falling within the scope of the appended claims. Certain definitions and descriptions may be specifically detailed in particular steps of methods described herein, but it is understood that these same principles and applications apply to other steps with similar references, and are not limited to the particular steps described.

The disclosed embodiments improve upon the problems with the prior art by providing a system and method that offers a holistic approach to comprehensively assessing a user's performance during medical procedures. Unlike some existing systems that may focus solely on either physiological or biomechanical metrics, this method integrates both types of metrics. By considering both the physical movements and the physiological responses of the user, the system can provide a nuanced evaluation that better reflects the complexities of performing medical procedures.

The method utilizes advanced machine learning algorithms, including neural networks, to continuously train and refine the assessment model based on new data. This dynamic approach allows the system to evolve and adapt to new techniques and standards in medical procedures, ensuring that the training remains relevant and up-to-date. This contrasts with some prior art methods that may rely on static models which do not evolve once initially programmed.

The system not only identifies deviations from performance benchmarks during the medical procedures but also provides real-time feedback to the user. This feedback can be delivered through various modalities including haptic (tactile), auditory, and visual signals. This immediate feedback is crucial for learning and correcting techniques on the fly, which is a significant improvement over systems that provide feedback only after the completion of the procedure.

By identifying different procedural segments and associating specific benchmarks with each, the method allows for detailed performance analysis. It can pinpoint not just overall performance but also segment-specific areas of improvement. This segmented approach is particularly useful in complex medical procedures that require a series of steps to be executed with high precision.

The method includes steps for sensor calibration and the use of spatial reference points to ensure accuracy in data collection. This feature is vital as it enhances the reliability of the measured metrics by accounting for individual differences in sensor placement and user movement patterns. This level of precision in tracking and measurement is often lacking in less sophisticated systems.

By focusing on these improvements, the method enhances the effectiveness of training medical professionals, offering a more detailed and adaptive learning tool compared to existing technologies. These improvements not only contribute to the personal development of healthcare providers but also potentially increase the overall safety and efficacy of medical procedures performed on patients.

Referring now to the Figures, FIG. 1 is a diagram of an operating environment that supports a system for providing non-repudiation of communications online between a plurality of users over a communications network in accordance with the principles of the present invention, according to an example embodiment. The most prominent element of FIG. 1 is the server 102 associated with repository or database 104 and further coupled with network 106, which can be a circuit switched network, such as the Public Service Telephone Network (PSTN), or a packet switched network, such as the Internet or the World Wide Web, the global telephone network, a cellular network, a mobile communications network, or any combination of the above. In one embodiment, network 106 is a secure network wherein communications between endpoints are encrypted so as to ensure the security of the data being transmitted. Server 102 is a central controller or operator for the functionality that executes on at least a user computing device 114, via various methods.

FIG. 1 further includes a user computing device 114 and a second user computing device 122, which each may be smart phones, mobile phones, tablet computers, handheld computers, laptops, or the like. The user computing device 114 corresponds to the user 110. Second user computing device 122 corresponds to second user 120. Each of the computing devices include a user interface and/or graphical user interface. In certain embodiments, the system may communicate between the user, the second user, over the communications network, where the user is medical professional performing a medical procedure, and the second user is a medical supervisor.

FIG. 1 also shows a wearable device 112, which may include, but is not limited to, smartwatches, fitness trackers, chest straps, smart clothing, and sensor-embedded gloves. The wearable device 112 corresponds to the user. These devices are equipped with sensors such as accelerometers, gyroscopes, heart rate monitors, electromyography (EMG) sensors, and possibly even more specialized sensors like electroencephalography (EEG) or near-infrared spectroscopy (NIRS) for measuring brain activity and muscle oxygenation respectively. The wearable devices interact with the system by continuously or periodically collecting data during the performance of medical procedures. The collected data includes both physiological parameters (such as heart rate, skin temperature, and muscle activity) and biomechanical parameters (such as movement patterns, posture, and force exertion). This data is then transmitted to a central computing system where it is analyzed to train algorithms, identify procedural segments, and benchmark performance metrics. While the wearable device mainly communicates with the server, the wearable device may also communicate with user computing device 114 and the second user computing device 122.

FIG. 1 further shows that server 102 includes a database or repository 104, which may be one or more of a relational databases comprising a Structured Query Language (SQL) database stored in a SQL server, a columnar database, a document database and a graph database. Computing devices 114 and 122 may also each include their own database. The repository 104 serves data from a database, which is a repository for data used by server 102 and the mobile devices during the course of operation of the invention. Database 104 may be distributed over one or more nodes or locations that are connected via network 106.

The software is configured to create records for the users. The database 104 may include a stored record for each of the users in the system. The database may be configured to store a subset of user attributes including non personal identifying information ("PII") data. PII means information that identifies, relates to, describes, is capable of being associated with, or could reasonably be linked, directly or indirectly, with a particular user. Non PII data may include information that is anonymous and cannot identify the user. Non PII data helps protect the user such that the information may not be used to harm the user. Non PII data may include device type, browser type, language preference, time zone, etc.

FIG. 1 shows an embodiment wherein networked computing devices 114 and 122 may interact with server 102 and repository 104 over the network 106. Server 102 includes a software engine that delivers applications, data, program code and other information to networked computing devices 114 and 122. The software engine of server 102 may perform other processes such as audio and/or video streaming or other standards for transferring multimedia data in a stream of packets that are interpreted and rendered by a software application as the packets arrive. It should be noted that although FIG. 1 shows only two networked mobile computing devices 114 and 122, the system of the present invention supports any number of networked mobile computing devices connected via network 106, having at least the user computing device 114 and the second user computing device 122.

Server 102 also includes program logic comprising computer source code, scripting language code or interpreted language code that is compiled to produce executable file or computer instructions that perform various functions of the present invention. In another embodiment, the program logic may be distributed among more than one of server 102, computing devices 114 and 122, or any combination of the above.

Note that although server 102 is shown as a single and independent entity, in one embodiment of the present invention, the functions of server 102 may be integrated with another entity, such as each of computing devices 114 and 122. Further, server 102 and its functionality, according to a preferred embodiment of the present invention, can be realized in a centralized fashion in one computer system or in a distributed fashion wherein different elements are spread across several interconnected computer systems. While the blockchain is illustrated as a single entity, the blockchain is actually decentralized, meaning that the data in the blockchain is stored into multiple nodes of the network. The decentralized nature of the blockchain allows the data stored within the blockchain to be immutable.

Figure 3C:
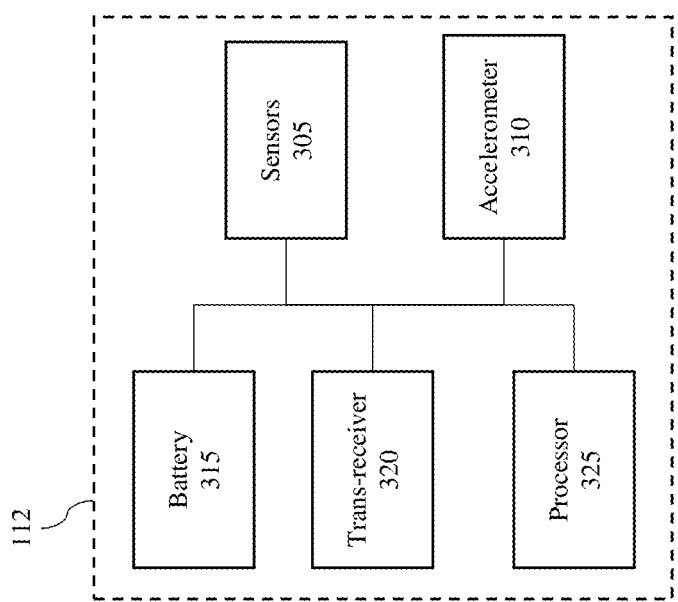
FIG. 3C is a block diagram illustrating the electrical components of the wearable device, according to an example embodiment.

With reference to FIGS. 3A through 3C, a wearable device is illustrated, according to an example embodiment. The wearable device includes a battery 315, sensors 305, a processor 325, a trans-receiver 320, and an accelerometer 310. A battery is a device that stores and supplies electrical energy to power the wearable device. In the wearable device, the battery may be a rechargeable lithium-ion or lithium-polymer battery due to their high energy density and compact size. It is integrated into the housing of the device, situated to balance weight distribution for user comfort. The sensors are devices that detect and measure specific physical or biological parameters. The wearable device may include multiple sensors such as optical heart rate sensors, EMG sensors, temperature sensors, and galvanic skin response (GSR) sensors. These sensors are strategically placed to ensure accurate data collection. For instance, the EMG sensors are located on the underside of the device to maintain contact with the skin. Advanced sensors provide real-time data that is important for precise performance evaluation and feedback. The processor is the central unit that processes data collected by the sensors. The processor, possibly a low-power microcontroller or system on a chip (SoC), is embedded within the main body of the device. It handles data processing tasks such as signal filtering, analysis, and algorithm execution. The trans-receiver is a device that transmits and receives data wirelessly. The trans-receiver is integrated within the device to facilitate communication with external systems like computers or smartphones. It allows for the seamless transfer of data collected by the sensors to a central processing unit for further analysis. The accelerometer is a sensor that measures acceleration forces, providing data on movement and orientation. The accelerometer is embedded within the device to capture data on wrist movements and overall activity levels. It works in conjunction with other sensors to analyze the biomechanical aspects of the user's performance.

The sensors and accelerometer collect a plurality of measured metrics while worn by the user. The measured metrics include physiological parameters and biomechanical parameters measured during each of the plurality of training medical procedures. Physiological parameters refer to the biological data that reflect the internal state of the body, such as heart rate, muscle activity, and skin temperature. Biomechanical parameters refer to the mechanical aspects of movement, such as the speed, angle, and force of the user's motions. Measured metrics refer to quantifiable data points collected from various sensors and devices, capturing a wide range of physiological, biomechanical, and environmental parameters. These metrics are used to assess, monitor, and analyze performance, health, and environmental conditions across different contexts and applications, such as medical procedures, athletic performance, and industrial operations. This data is used to evaluate the user's performance, identify procedural segments, and compare against predefined benchmarks to provide real-time feedback and improve proficiency.

Physiological parameters provide insight into the user's bodily functions and responses during the training procedures. Main physiological parameters may include, but are not limited to, heart rate, heart rate variability ("HRV"), electromyography ("EMG") activity, skin temperature, and galvanic skin response ("GSR"). Heart rate is measured to assess cardiovascular activity, indicating how the user's heart responds to the physical and mental demands of the procedure. HRV evaluates the variations between heartbeats, providing data on the user's stress and recovery levels. EMG activity measures the electrical activity produced by skeletal muscles, indicating which muscles are engaged, the intensity of their contractions, and muscle fatigue. Skin temperature is monitored to assess changes in the user's body temperature, which can reflect physical exertion and emotional stress. GSR measures the electrical conductance of the skin, which varies with its moisture level, providing data on the user's stress and emotional arousal.

Biomechanical parameters provide data on the physical movements and forces exerted by the user during the medical procedures. Main biomechanical parameters may include, but are not limited to, accelerometry, gyroscopic data, joint angles, force exertion, and movement patterns. Accelerometry captures the acceleration of the user's movements, providing data on the speed and direction of hand and arm motions. Gyroscopic data measures the angular velocity and orientation of the user's limbs, providing detailed information on rotational movements and positioning. Joint angles monitors the angles at which joints, such as the wrist, elbow, and shoulder, are positioned during various stages of the procedure. Force exertion measures the amount of force applied by the user's hands and arms, indicating the effort and precision required during specific tasks. Movement patterns track the trajectory and coordination of the user's motions, identifying the efficiency and fluidity of their movements.

Figure 4:
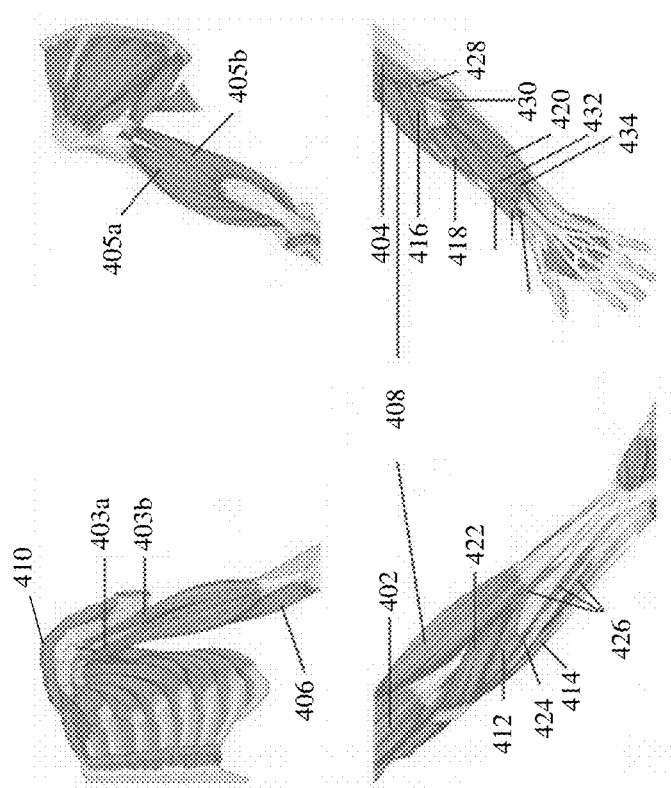
FIG. 4 is a diagram of the muscles of an arm and a hand, according to an example embodiment.

With reference to FIG. 4, a diagram illustrating the muscles within an arm and hand is shown, according to an example embodiment. Arm and hand movements involve a complex interplay of various muscles that coordinate to achieve precise actions. The muscles of the arm include the biceps brachii 402, triceps brachii 404, brachialis 406, brachioradialis 408, and deltoid 410. The biceps brachii, a two-headed muscle located on the front of the upper arm, is responsible for flexion of the elbow and supination of the forearm. The biceps brachii include a short head 403*a* and a long head 403*b*. It contracts to lift the forearm and rotate it during tasks like lifting objects or turning a doorknob. The triceps brachii, located on the back of the upper arm, is a three-headed muscle responsible for extension of the elbow, essential for pushing movements or throwing. The triceps brachii include a lateral head 405*a* and long head 405*b*. The brachialis, situated beneath the biceps brachii, primarily facilitates elbow flexion, working synergistically with the biceps brachii in lifting and carrying actions. The brachioradialis, a forearm muscle extending from the humerus to the radius, aids in elbow flexion, particularly when the forearm is in a mid-prone position. Lastly, the deltoid, a large triangular muscle covering the shoulder, enables abduction, flexion, extension, and rotation of the arm at the shoulder joint, contributing to various arm movements and stabilizing the shoulder.

The forearm muscles include the flexor carpi radialis 412, flexor carpi ulnaris 414, extensor carpi radialis longus 416 and *brevis* 418, extensor carpi ulnaris 420, and pronator teres 422. The flexor carpi radialis, located on the anterior side of the forearm, flexes and abducts the wrist, while the flexor carpi ulnaris flexes and adducts the wrist. The extensor carpi radialis longus and *brevis*, found on the posterior side of the forearm, extend and abduct the wrist, whereas the extensor carpi ulnaris extends and adducts the wrist. The pronator teres, situated on the anterior forearm, pronates the forearm, actively rotating it so the palm faces down, as seen when turning a key. Other forearm muscles include the palmaris longus 424, flexor digitorum superficial muscles 426, lateral epicondyle of humerus 428, anconeus 430, extensor digitorum 432, and extensor digiti minimi 434.

The hand muscles are important for fine motor tasks and include the flexor digitorum superficialis, flexor digitorum profundus, extensor digitorum, flexor pollicis longus, and thenar muscles. The flexor digitorum superficialis, on the anterior side of the forearm extending into the hand, flexes the fingers at the proximal interphalangeal joints, essential for gripping actions. The flexor digitorum profundus, a deeper muscle, flexes the fingers at the distal interphalangeal joints, working with the flexor digitorum superficialis to enable strong gripping and fine motor tasks. The extensor digitorum, located on the posterior forearm, extends the fingers, aiding in opening the hand and spreading the fingers. The flexor pollicis longus, found on the anterior forearm, flexes the thumb, playing a crucial role in pinching and grasping movements. Finally, the thenar muscles, a group of muscles at the base of the thumb, control the thumb's movement, including opposition, flexion, abduction, and adduction, essential for thumb dexterity and performing precise grips.

The wearable device may include sensors, such as, but not limited to, EMG, pressure and force, and/or flex sensors, configured to detect and measure movements of the muscles describe herein. Other muscles may also detected and measured by the sensors within the wearable device and are within the spirit and scope of the present invention. This data collected from the sensors are stored as physiological parameters and the biomechanical parameters.

Figure 2:
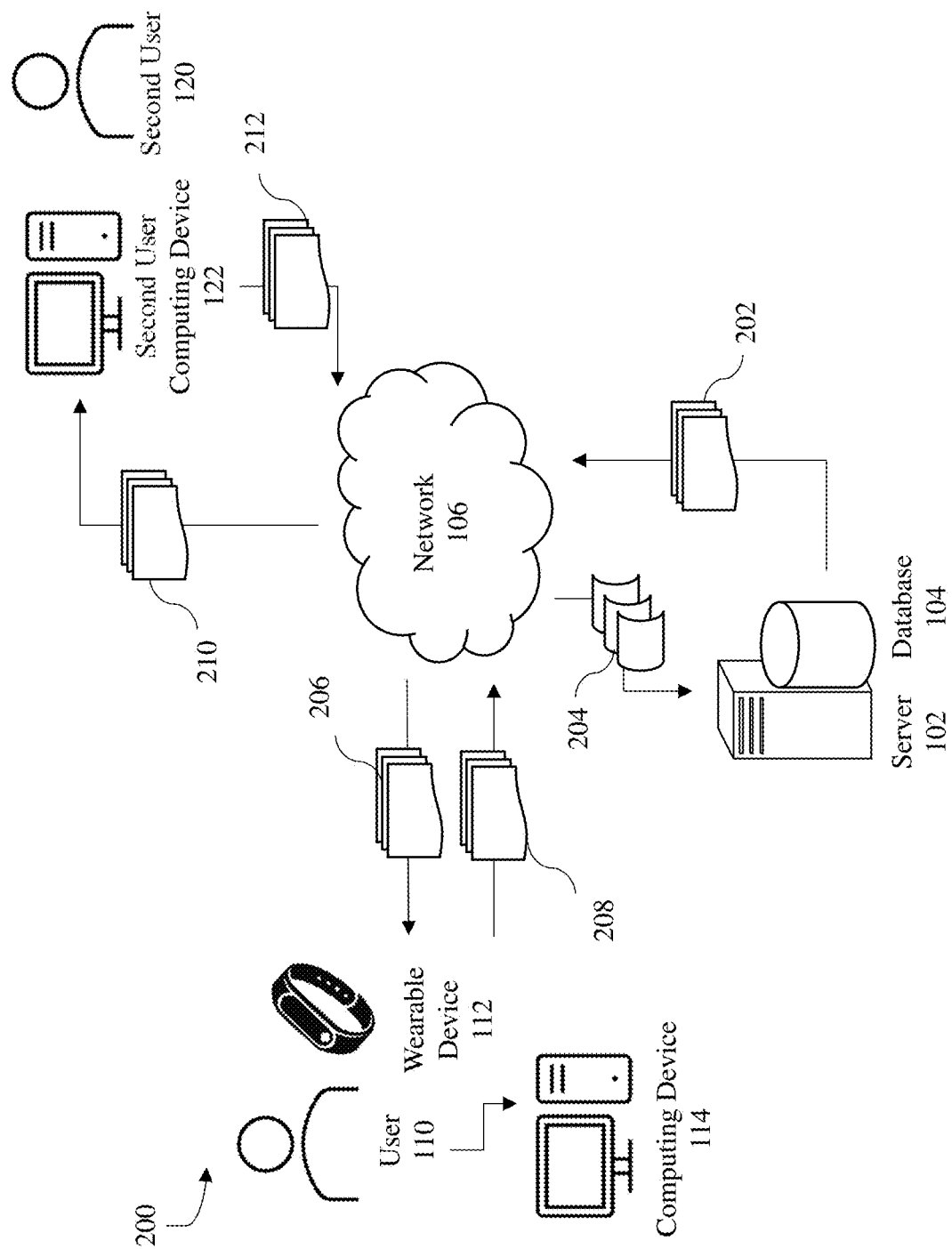
FIG. 2 is a schematic illustrating communication between the entities in FIG. 1 in relation to evaluating a user's performance of a medical procedure, according to an example embodiment.

The process for evaluating a user's performance of a medical procedure will now be described with reference to FIGS. 2 and 5 through 7. FIGS. 2 and 5 through 7 depict, among other things, data flow and control flow in the process for evaluating a user's performance of a medical procedure, according to one embodiment. FIG. 2 is a schematic 200 illustrating communication between the entities in FIG. 1 in relation to evaluating a user's performance of a medical procedure, according to an example embodiment. It is understood that in FIG. 2, the data packets 202, 204, 206, 208, 210, and 212 are used to show the transmission of data and may be used at different stages of the process. The user 110 may use the user computing device 114 to communicate with the server 102 and the second user computing device 122. The server 102 may provide graphical user interfaces to each of the user computing device, second user computing device, and, in some embodiments, the wearable device 112. The graphical user interfaces described herein may be displayed by any of the user computing device, second user computing device, and, in some embodiments, the wearable device 112. Each of the graphical user interfaces may be configured to allow the user to interact with the interface, and/or webpage, such that the interface(s) and display(s) may include a plurality of user interface elements such as input controls, navigation components, informational components, and containers. Such user interface elements may include for example, accordions, bento menu(s), breadcrumb(s), button(s), card(s), carousel(s), check box (es), comment(s), doner menu(s), dropdown(s), feed(s), form(s), hamburger menu(s), icon(s), input field(s), kebab menu(s), loader(s), meatball menu(s), modal(s), notification (s), pagination(s), picker(s), progress bar(s), radio button(s), search field(s), sidebar(s), slide control(s), stepper(s), tag(s), tab bar(s), tool tip(s), and toggle(s). Each of these user interface elements may be used in certain embodiments to enable each of the users to interact with the system, provide data to and from the server across the communications network and implement the methods as discussed in FIGS. 5A through 7. Other user interface elements configured to provide a display to the user to interact with the system in accordance with the methods described herein may be used and are within the spirit and scope of the disclosure. The user may interact with the graphical user interfaces using computer gestures to trigger certain elements on the graphical user interfaces. A computer gesture may include gestures such as a tap, via a touch sensitive interface display, a click, on or near one of the second user graphical indicators.

Figure 5A:
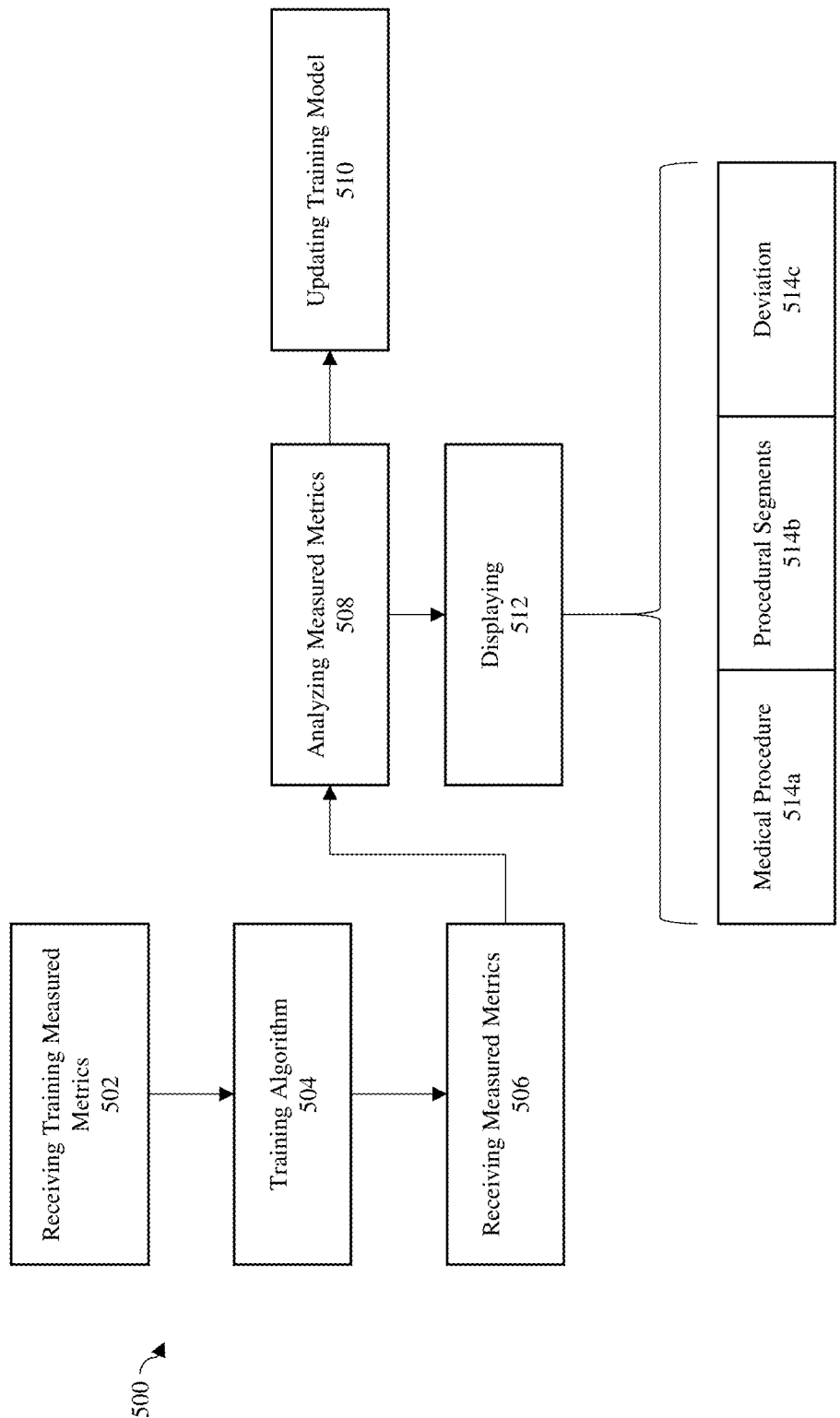
FIG. 5A is a flowchart diagram illustrating steps for a method for analyzing the plurality of measured metrics collected during the medical procedure, according to an example embodiment.

Referring now to FIG. 5A, a computer-implemented method 500 for evaluating a user's performance of a medical procedure is shown, according to an example embodiment. Method 500 begins with step 502, wherein the server 102 receives a plurality of training measured metrics collected from a sensor worn by the user while performing a plurality of training medical procedures. The wearable device receives training measured metrics from the user 110 while performing a medical procedure The trans-receiver of the wearable device sends training measured metrics via data packet 208 to the network 106, which sends said training measured metrics to the server via data packet 204.

Then, in step 504, method 500 includes training, based on the plurality of training measured metrics collected during the plurality of training medical procedures, an algorithm to identify types of training medical procedures, procedural segments for each of the types of training medical procedures, and a performance benchmark for each of the plurality of types of training medical procedures. The algorithm is trained to recognize different types of medical procedures based on the collected metrics. Machine learning techniques are employed where the collected data is labeled with the type of procedure performed. The algorithm learns to distinguish between different procedures by identifying unique patterns and signatures in the data. The algorithm can classify an unknown set of metrics into one of the predefined types of medical procedures. The algorithm is also trained to segment each type of medical procedure into its constituent stages or steps. The collected data is annotated to indicate different segments within each procedure. For instance, a surgical procedure might be divided into preparation, incision, suturing, and closure stages. The algorithm uses this annotated data to learn how to segment procedures by recognizing transitions between different stages based on changes in the metrics. The algorithm can identify and segment a medical procedure into its respective stages in real-time as the data is received. The algorithm is further trained to establish performance benchmarks for each type of medical procedure. Performance benchmarks are derived by analyzing the data from multiple users performing the same procedures under similar conditions. Metrics such as average completion time, precision of movements, and physiological responses are aggregated to define the benchmarks. These benchmarks represent the optimal or standard performance for each procedure. The algorithm can compare a user's performance against these benchmarks to evaluate their proficiency and identify areas for improvement.

This approach provides a more detailed and objective analysis of medical procedures compared to traditional methods, which often rely on subjective assessments and limited metrics. By leveraging a wide range of physiological and biomechanical data, the algorithm can provide a nuanced and comprehensive evaluation of performance, leading to more effective training and feedback.

In some embodiments, said training includes using a training model including a neural network in conjunction with at least one machine learning algorithm to analyze the plurality of training measured metrics collected during the plurality of training medical procedures. The system uses the neural network to identify at least one type of medical procedure of the plurality of types of training medical procedures, at least one of the plurality of procedural segments, and the performance benchmark for the at least one type of medical procedure of the plurality of types of training medical procedures. The training model is an advanced computational framework that combines the strengths of neural networks and machine learning algorithms. It processes and learns from a large dataset of training measured metrics to develop a nuanced understanding of various medical procedures and their performance benchmarks.

A neural network is a computational model inspired by the human brain's structure and function. It consists of layers of interconnected nodes (neurons) that process input data, learn patterns, and make predictions. Machine learning algorithms are a set of algorithms that enable the model to learn from data, identify patterns, and make decisions based on that learning. Common algorithms include supervised learning methods like support vector machines (SVM), decision trees, and unsupervised learning methods like clustering algorithms. Labeled training data, where each dataset is tagged with the type of medical procedure performed, is fed into the neural network. Through multiple iterations and adjustments, the network learns to distinguish between different procedures based on the unique patterns in the physiological and biomechanical data. The training data is annotated with labels indicating different procedural segments. The neural network, possibly in conjunction with algorithms like hidden Markov models (HMM) or recurrent neural networks (RNNs), learns to identify transitions between segments based on changes in the collected metrics. The machine learning algorithms analyze the training data to determine average performance metrics for each procedural segment. Metrics such as average time, precision, force applied, and physiological responses are calculated and set as benchmarks. For example, in laparoscopic surgery training, the neural network might use accelerometer and EMG data to learn movement patterns associated with different surgical steps, such as incision, dissection, and suturing. Machine learning algorithms analyze this data to establish benchmarks for movement precision and muscle activity, which the model uses to evaluate new training sessions.

Next, in step 506, method 500 further includes receiving, from the sensor worn by the user while performing the medical procedure, a plurality of measured metrics. Similarly to the training measured metrics, the measured metrics include the physiological parameters and the biomechanical parameters. The wearable device receives measured metrics from the user 110 while performing a medical procedure. The trans-receiver of the wearable device sends measured metrics via data packet 208 to the network 106, which sends said measured metrics to the server via data packet 204.

Then, in step 508, method 500 includes analyzing the plurality of measured metrics collected during the medical procedure so as to identify the medical procedure as one of the plurality of types, the plurality of procedural segments of the medical procedure, and a deviation between the performance benchmark and the plurality of measured metrics collected during the medical procedure. This creates a procedural profile for the user. The system applies machine learning algorithms trained on historical data to recognize patterns in the measured metrics that correspond to different types of medical procedures. Using techniques such as support vector machines (SVM), neural networks, or decision trees, the system compares the real-time data with the trained model to classify the procedure. For example, the system may identify a procedure as a laparoscopic appendectomy based on the specific movement patterns, force application, and physiological responses typical of this procedure. The system further analyzes the data to segment the procedure into its distinct phases or steps. This may be done using algorithms like hidden Markov models (HMM) or dynamic time warping (DTW). The system identifies key procedural segments such as preparation, incision, dissection, suturing, and closure. For example, during a laparoscopic appendectomy, the system may segment the procedure into steps like trocar insertion, appendix isolation, appendix removal, and suturing.

For each identified segment, the system compares the real-time measured metrics against established performance benchmarks. These benchmarks are derived from training data and represent optimal performance standards. The system calculates the deviation for each metric by determining the difference or percentage difference between the measured values and the benchmarks. The deviations calculated may include time taken, precision of movements, forces applied, and physiological responses. For example, the system may compare the time spent on each segment against the benchmark time, assess the accuracy of movements using metrics like movement path deviations, and/or measure the force exerted and comparing it to the optimal force range. The system may aggregate these deviations to provide an overall performance assessment for each segment and the entire procedure. For example, if the benchmark for incision depth is 1 cm with a ±0.2 cm tolerance, and the measured depth is 1.3 cm, the deviation is 0.3 cm, indicating a need for correction.

The aggregate of the plurality of sets of metrics refers to the comprehensive compilation and synthesis of multiple datasets, each comprising measured metrics collected from various users during the performance of medical procedures. These datasets encompass a wide array of physiological and biomechanical parameters, including but not limited to heart rate, electromyography (EMG) activity, movement patterns, joint angles, and force exertion. The aggregation process involves normalizing individual datasets to ensure consistency across different users and conditions, followed by the integration of these normalized datasets into a unified dataset. This aggregate dataset serves as a robust and comprehensive pool of metrics that can be analyzed to establish standard benchmarks of performance. The benchmarks are derived by statistically analyzing the aggregate data to identify common patterns, averages, and deviations that define optimal performance standards. These benchmarks provide a reference framework against which individual performances can be compared, facilitating the identification of deviations and the provision of targeted feedback to improve proficiency in medical procedures.

The aggregate of the plurality of sets of metrics can be analyzed using various statistical tests and machine learning algorithms to derive meaningful insights and establish standard benchmarks of performance. For instance, k-means clustering can be employed to partition the aggregate data into distinct clusters based on the similarity of measured metrics, thereby grouping similar performance patterns together and identifying common procedural techniques and variations among users. Principal Component Analysis (PCA) reduces the dimensionality of the dataset while preserving the most critical variance, enabling the extraction of key metrics that define optimal performance benchmarks. Analysis of Variance (ANOVA) tests can determine if there are statistically significant differences between the performance metrics of different user groups or procedural segments, highlighting which aspects of the procedure or user characteristics most significantly impact performance. Linear regression analysis models the relationship between dependent and independent variables, predicting performance outcomes based on specific measured metrics, such as correlating muscle activity levels with surgical precision. t-tests and paired t-tests compare the means of different groups or the same group over time to validate training program effectiveness and performance improvements. Time series analysis examines data points collected over time to identify trends and cycles in performance metrics, establishing benchmarks for expected skill progression. Hierarchical clustering builds a hierarchy of clusters to understand the nested structure of performance data, refining benchmarks for different procedural complexities or user skill levels. Random forests and decision trees classify data and predict outcomes, identifying which metrics are crucial for distinguishing between high and low performers. These analyses collectively enable the comprehensive examination of the aggregate metrics, leading to the establishment of robust, data-driven benchmarks for evaluating and improving medical procedural training and execution.

By way of example, in a laparoscopic surgery training session, the system recognizes the procedure as a laparoscopic appendectomy and segments the procedure into steps like trocar insertion, dissection, and suturing. The system then compares the user's performance in each segment against the benchmarks, identifying that the user's suturing is slower than the optimal time and that the force applied during dissection is too high. This real-time, detailed analysis offers significant improvements over traditional training methods, which often rely on post-procedure reviews and subjective assessments. The ability to continuously monitor, segment, and compare performance against benchmarks provides objective, actionable feedback, leading to more effective training and faster skill acquisition.

Analyzing the plurality of measured metrics with the aggregate of the plurality of measured metrics involves a methodical process, beginning with retrieving the aggregate metrics from a stored database. The aggregate metrics, which are normalized and compiled from multiple users and sessions, serve as the standard benchmarks for performance evaluation. The system queries the database to access these benchmarks corresponding to the specific type of medical procedure and its procedural segments. A deviation is then calculated, defined as the difference between the current measured metrics collected in real-time from the user and the benchmark metrics derived from the aggregate data. This deviation quantifies the extent to which the user's performance metrics diverge from the established standards, providing a basis for evaluating and improving performance.

The deviation between the measured metrics and the benchmark metrics is a critical indicator of performance quality, quantifying the difference between real-time metrics collected from the user during a medical procedure and the established benchmarks derived from aggregate data. This deviation is calculated using various mathematical methods, such as absolute difference, percentage difference, or standard score (Z-score), depending on the type of metric and required precision. For instance, the deviation in heart rate might be calculated as the absolute difference between the measured heart rate and the benchmark heart rate, while the deviation in force applied could be expressed as a percentage difference from the benchmark force. By identifying specific areas where the user's performance diverges from expected standards, the system provides real-time feedback to correct techniques and improve proficiency.

Further analysis includes comparing the measured metrics using machine learning techniques. This process may involve converting the measured metrics into embeddings, which are dense vector representations of the data. These embeddings are then plotted as clusters within a network of clusters, where each cluster stored in the database represents a benchmark, procedural segment, or type of procedure. The current cluster, formed by the real-time measured metrics, is compared to the stored clusters to identify relationships and similarities. This comparison helps in determining how closely the user's current performance aligns with the benchmarks and segments defined by the aggregate data. The machine learning analysis leverages these relationships to identify specific procedural segments and provide detailed insights into performance, facilitating targeted feedback and training improvements.

The system employs advanced machine learning techniques to analyze the measured metrics collected during a medical procedure by converting these metrics into embeddings and clustering them to facilitate the identification of procedural segments and overall performance evaluation. Embeddings, which are dense, continuous vector representations of the measured metrics, capture multiple dimensions such as heart rate, muscle activity, movement patterns, and force exerted. Each vector in the embedding space encapsulates these dimensions, preserving the intrinsic relationships and patterns within the data. The vectors importance lies in their ability to represent similar performance metrics as close proximities in the high-dimensional space, thereby enabling the identification of patterns and clusters.

The system processes the measured metrics through a neural network, which converts these raw data points into embeddings. The neural network, trained on extensive datasets, recognizes and preserves significant features and relationships within the metrics, ensuring accurate embedding representation. These embeddings are then plotted as clusters within a network of clusters, each representing a benchmark, procedural segment, or type of procedure. The system analyzes overlapping regions of these clusters to aid in identifying the segment being performed, based on similarities in the metrics. This clustering approach allows the system to determine how closely the user's current performance aligns with the established standards.

The system continuously updates, trains, and improves the neural network by incorporating new data from ongoing procedures, refining its understanding and accuracy over time. Each measured metric, whether physiological or biomechanical, contributes to the standard of performance by defining the expected range and variability for optimal procedure execution. In some embodiments, the stored metrics compared are derived from a pool of users, providing a broad benchmark based on diverse performance data. In other embodiments, the measured metrics are compared to the user's past performances, allowing for personalized benchmarking and targeted feedback based on the user's historical data. This continuous learning and adaptive benchmarking ensure that the system remains robust and relevant, providing precise and actionable insights to enhance procedural proficiency.

Next, in step 510, method 500 includes updating the training model based on the plurality of measured metrics collected during the medical procedure. Updating the training model entails incorporating new data collected during medical procedures into the existing model. This process allows the model to adjust its parameters, improve its predictive accuracy, and refine performance benchmarks based on the latest measurements. The new data is labeled with relevant information, such as the type of procedure and the specific procedural segments. This labeling helps in accurately updating the model. Key features are extracted from the new data, focusing on metrics that are most indicative of performance, such as the precision of movements, timing, and physiological responses.

The training model includes a neural network. The neural network is a computational model consisting of interconnected nodes, or neurons, organized into layers. These layers include an input layer, one or more hidden layers, and an output layer. Each node in one layer is connected to nodes in subsequent layers, with each connection assigned a weight. The neural networks is designed to recognize patterns, learn from data, and make decisions or predictions based on input data. They achieve this by adjusting the weights of the connections during a training process using algorithms like backpropagation, which minimizes the difference between predicted outputs and actual targets. This adjustment process allows neural networks to improve their performance over time as they are exposed to more data.

The neural network employs a plurality of machine learning algorithms, which are a set of methods and techniques that enable the processors and computers to learn from data, identify patterns, and make decisions with minimal human intervention. These algorithms can be broadly categorized into supervised learning, where the algorithm learns from labeled training data to make predictions or classifications; unsupervised learning, where the algorithm identifies patterns or groupings in unlabeled data; and reinforcement learning, where the algorithm learns by interacting with an environment and receiving feedback in the form of rewards or penalties. Examples of machine learning algorithms include linear regression, support vector machines, k-means clustering, and deep reinforcement learning. These algorithms are applied across various domains to solve complex problems by analyzing data and making informed decisions based on identified patterns and relationships.

The training model, which includes the neural network and machine learning algorithms, is retrained using the new data. This process involves feeding the annotated data into the model and allowing it to adjust its weights and biases based on the new information. Machine learning algorithms (e.g., support vector machines, clustering algorithms) update their parameters to incorporate the new data. This may involve adjusting decision boundaries, recalculating centroids in clustering, or updating probability distributions in probabilistic models. The updated model is validated using a separate validation dataset to ensure that the updates have improved its accuracy and performance. The model's predictions are compared against known outcomes to assess its reliability. The model may be tested in real-world scenarios to ensure that it accurately identifies procedural types, segments, and performance benchmarks based on the updated data. The process of updating the model is iterative. As more data is collected from subsequent medical procedures, the model continues to learn and refine its predictions and benchmarks. The model employs adaptive learning techniques to adjust its learning rate and parameters dynamically, ensuring it remains responsive to new data while avoiding overfitting.

The use of neural networks and machine learning algorithms to find patterns in procedural segments and between different procedures involves a detailed and sophisticated analysis process. During medical procedures, wearable devices collect a wide range of physiological and biomechanical metrics, such as heart rate, muscle activity, movement patterns, and force exertion. These metrics are processed through feature extraction algorithms to identify key characteristics relevant to each procedural segment. The extracted features are converted into vector embeddings using a neural network, which represent the high-dimensional relationships between different features in a compact form. Machine learning algorithms, such as k-means clustering or hierarchical clustering, are then applied to these embeddings to group similar data points together, with each cluster representing a distinct procedural segment, such as incision, dissection, or suturing. The system identifies patterns within these clusters, defining benchmarks for each segment based on typical performance characteristics.

The system employs the neural networks and machine learning algorithms to analyze measured metrics collected during medical procedures. Initially, wearable devices continuously gather a range of physiological and biomechanical metrics, such as heart rate, muscle activity, movement patterns, and force exerted. This raw data is preprocessed to remove noise and ensure consistency, involving normalization and segmentation based on time or specific procedural events. The system then applies feature extraction algorithms to identify significant characteristics from the data, such as the frequency and amplitude of muscle contractions, movement speed and direction, and applied force.

Once features are extracted, the system converts these metrics into vector embeddings using a neural network. These embeddings are dense, continuous representations that encapsulate the high-dimensional relationships between different performance metrics. Machine learning algorithms, such as k-means clustering or hierarchical clustering, are applied to these embeddings to group similar data points, forming clusters that represent distinct procedural segments, like incision, dissection, or suturing. The system identifies patterns within these clusters to define benchmarks for each segment.

For comparing different procedures, the system matches the current data to pre-existing clusters in a database, each cluster representing a benchmark or procedural segment from various procedures, such as laparoscopic appendectomy or arthroscopic knee surgery. The system performs cross-procedure analysis to identify similarities and differences in performance requirements. It calculates deviations between the user's current performance metrics and established benchmarks to highlight areas needing improvement. Real-time feedback is provided to the user to facilitate immediate adjustments and continuous improvement. The neural network and machine learning models are continuously updated and retrained with new data, enhancing their accuracy and relevance. In some embodiments, the system compares the current metrics to a pool of data from multiple users, establishing broad benchmarks, while in others, it compares metrics to the user's past performances, creating personalized benchmarks. This comprehensive approach enables detailed performance analysis and helps users improve their proficiency in various medical procedures.

Next, in step 512, method 500 includes displaying, on a display, the medical procedure 514a as one of the plurality of types, the procedural segments 514b of the medical procedure; and the deviation 514c from the performance benchmark. The server sends data packet 202 including graphical user interface data to the network 106. The network 106 then sends data packet 210 including graphical user interface data to the second user computing device 122. The second user computing device processes the graphical user interface data and displays a graphical user interface for the second user. The graphical user interface data is configured to display information including the medical procedure 514a as one of the plurality of types, the procedural segments 514b of the medical procedure; and the deviation 514c from the performance benchmark. This allows the second user to evaluate the performance of the user that performed the medical procedure.

Figure 15A:
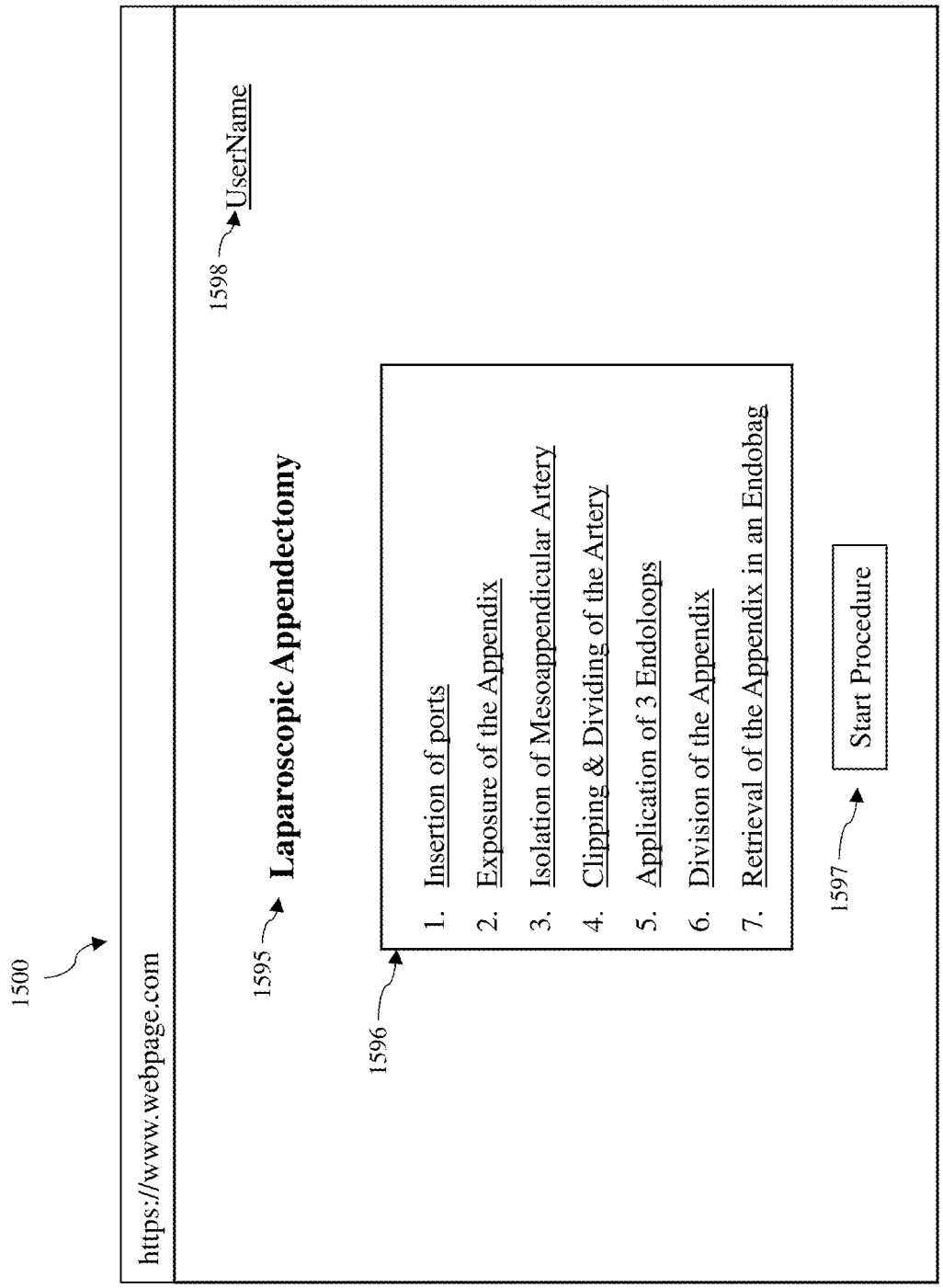
FIG. 15A illustrates a webpage including a procedure type and its procedural segments, according to an example embodiment.
Figure 15C:
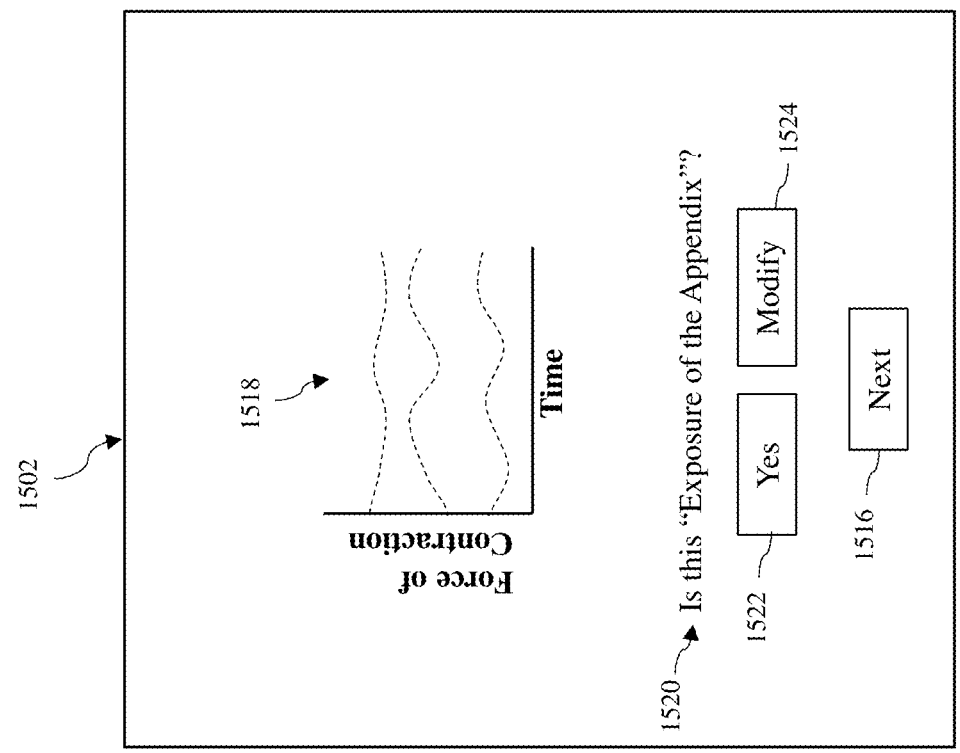
FIG. 15C illustrates a graphical user interface including the prediction of a second procedural segment, according to an example embodiment.
Figure 15B:
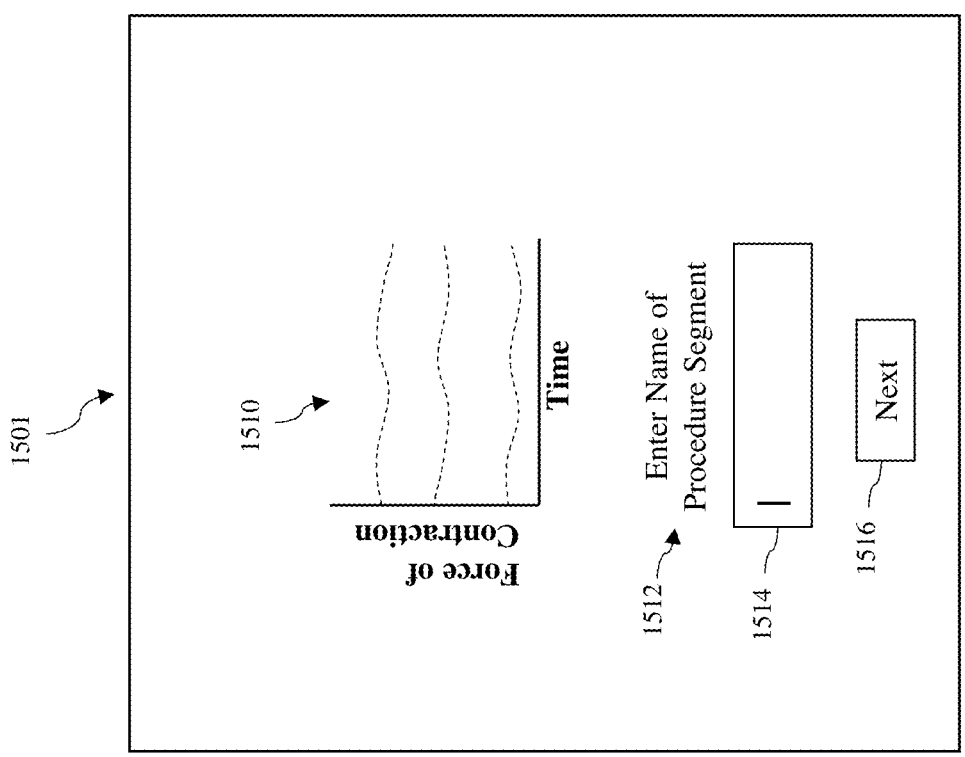
FIG. 15B illustrates a graphical user interface for training the algorithm, according to an example embodiment.
Figures 15D, 15E:
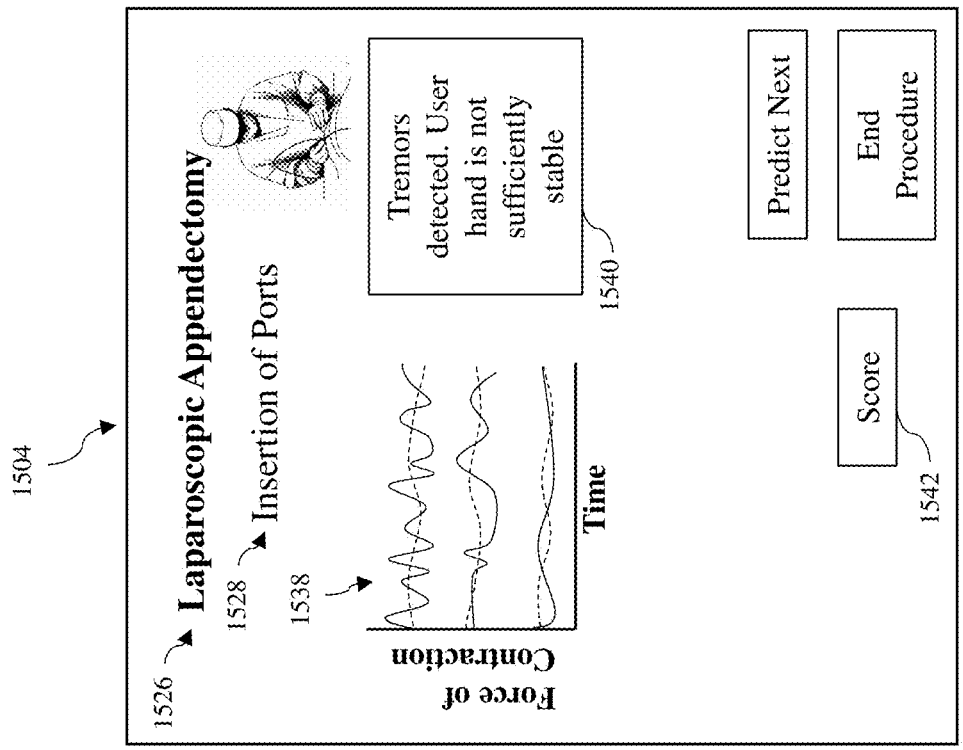
FIG. 15D illustrates a graphical user interface including a procedural segment, according to an example embodiment.
FIG. 15E illustrates a graphical user interface including a procedural segment and measured metrics, according to an example embodiment.

In one example embodiment, shown in FIG. 15D and FIG. 15E, graphical user interfaces 1503 and 1504, respectively, are configured to be displayed on the computing devices. Interfaces 1503 and 1504 display the type of medical procedure 1526 and a procedural segment 1528 of the medical procedure. The interfaces may also include a graphical representation 1530 corresponding to the currently displayed segment. While, in some embodiments, the system can predict the start and end of a procedural segment after its been trained, the interfaces 1503 and 1504 may include buttons 1532, 1534 that allow the user to indicate the start and end of a segment.

Interface 1503 includes a button 1536 that, when pressed, causes the system to display interface 1504 on the computing device. Interface 1504 displays measured metrics 1538 for the current procedural segment 1528 along with feedback 1540 from the system. For example, if the measured metrics include the forces of contractions over time, the system may be able to detect irregularities that indicate hand tremors of the user during the procedural segment. Interfaces 1503, 1504 further displays a button 1542 configured to allow the user or second user to assign a score to the measured metrics of the currently display segment.

In some embodiments, interacting with score button 1542 causes the system to display graphical user interface 1506, shown in FIG. 15G. Interface 1506 displays the name of the procedural segment 1528 and its graphical representation 1530. The interface 1506 further displays a table chart 1548 of example measured metrics and its respective deviations from the performance benchmarks. The table chart also includes the total deviation of the procedural segment, which is the aggregate of the deviations of the measured metrics. The deviations are calculated by the system. Interface 1506 also includes a prompt 1550 that asks the user or second user to assign a score for the performance of the user during the corresponding procedural segment. Input box 1552 allows the user or second user to input said score. The system may further calculate a suggested score 1554 based on the deviations and performance benchmarks. This score is displayed by the interface 1506, helping the user or second user assign an accurate score.

FIG. 15H illustrates a graphical user interface 1507, which is similar to interface 1506. However, interface 1507 is configured to be displayed after the user completes the medical procedure. Interface 1507 displays the name 1556 of medical procedure. Interface 1507 displays a table chart 1558 including example measured metrics and its respective deviations from the performance benchmarks. The deviations in chart 1558 are based on the aggregate of each procedural segment of the procedure. Interface 1507 also includes a prompt 1560 that asks the user or second user to assign a score for the overall performance of the user during the entire medical procedure. Input box 1562 allows the user or second user to input said score. The system may further calculate a suggested score 1564 based on the deviations and performance benchmarks. This score is displayed by the interface 1507, helping the user or second user assign an accurate score.

Figure 15F:
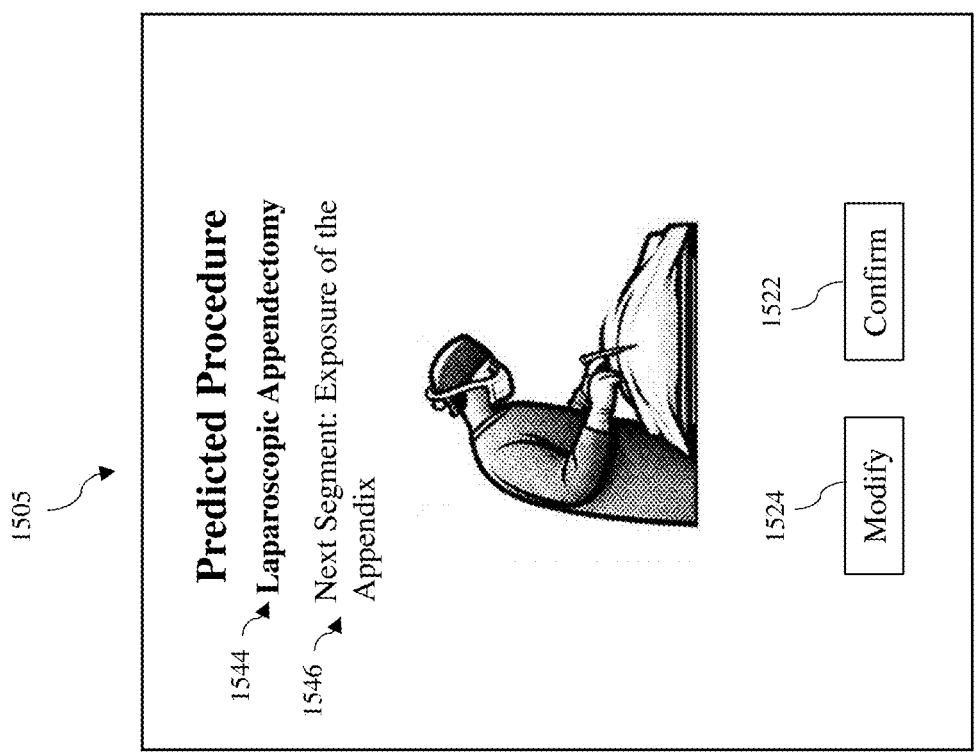
FIG. 15F illustrates a graphical user interface including the type of procedure predicted by the system, according to an example embodiment.
Figure 15I:
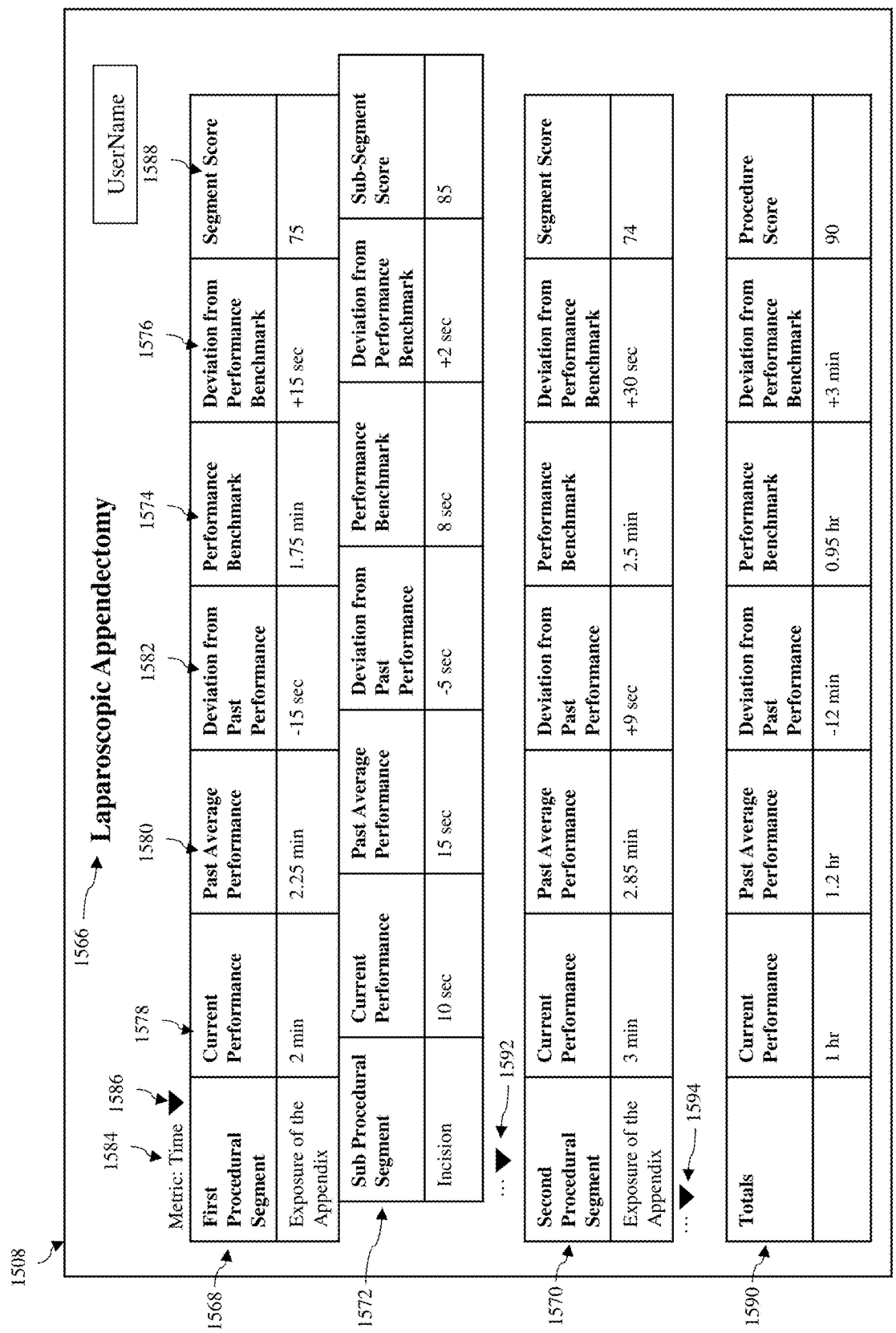
FIG. 15I illustrates a graphical user interface including measured metrics and deviations for a type of procedure and its procedural segments, according to an example embodiment.

In another example embodiment, shown in FIG. 15I, graphical user interface 1508 is configured to be displayed for the user computing device and/or second computing device. Interface 1508 displays the overall measured metrics of the user's performance for all segments of the medical procedure. The name 1566 or type of the procedure may be prominently displayed at the top of the screen or in a designated area, ensuring it is immediately visible to the user or observer. For example, "Laparoscopic Appendectomy" may be displayed as the procedure type. The procedural segments, such as first segment 1568, second segment 1570, etc., may be displayed in a sequential or timeline format, using a graphical representation such as a flowchart, timeline, segmented bar, or, in this case, a table chart. Each segment may include sub-segments 1572, each of which is labeled with its specific name, such as "Incision," "Dissection," "Suturing," etc. As the user progresses through the procedure, the display may dynamically update to highlight the current segment being performed. This can be indicated by changing colors, bolding the current segment, or using an animation to show progression. For each procedural segment, the display shows the performance benchmarks 1574, which are established standards or optimal performance metrics derived from previous data. The system calculates the deviation 1576 of the user's current performance 1578 from these benchmarks. This includes metrics such as time taken, precision of movements, force applied, and physiological responses. Other performance metrics related to medical procedures may be included and are within the spirit and scope of the present disclosure. The deviation from the performance benchmark may be visually represented using various methods, such as, but not limited to, numerical values, graphs and charts, color coding, and alerts and notifications.

Interface 1508 further displays the average metrics from the past performances 1580 of the same procedure and the deviation 1582 from those average metrics. This allows the user to see whether they are improving or not based on their past performances. The table chart may be filtered by metric type 1584 using the drop-down button 1586. This filtering option provides detailed statistics for the user or second user to assess the user's performance in certain areas. The charts also include a score 1588, assigned by the system and/or second user, for the segments, sub-segments, and procedure. Near the bottom of the interface 1508, the chart for the total metrics 1590 for the procedure are displayed. Drop-down buttons 1592, 1594 allow the user to view metrics for additional sub-segments of each procedural segment.

For example, the graphical user interface may display numerical indicators showing exact deviations, such as "+10 seconds" or "−5% force", or colors indicating performance status, such as green for within acceptable limits, yellow for slight deviations, and red for significant deviations. This advanced visualization system provides immediate, actionable feedback, significantly improving the training and performance evaluation process. Unlike traditional methods that may rely on post-procedure analysis and subjective assessments, this system offers real-time, objective data, enabling users to make on-the-fly adjustments and improve their performance continuously. It is understood that the examples provided above are illustrative and is not an exhaustive list.

In some embodiments, method 500 may include providing real-time feedback to the user based on the deviation from the performance benchmark. The feedback is selected from haptic, auditory, and visual feedback modalities. Real-time feedback is the instantaneous communication of performance information to the user, aimed at highlighting deviations from established benchmarks and suggesting corrective actions. The wearable device may be equipped with haptic actuators (e.g., vibration motors) that generate specific vibration patterns to signal the user. Different intensities and patterns of vibrations are used to indicate the severity and type of deviation. For example, a gentle vibration might signal a minor deviation, while a stronger, pulsing vibration could indicate a significant error. During a surgical procedure, if the user applies too much force while suturing, the device might vibrate to alert them to reduce pressure.

The system may generate audio signals (e.g., beeps, spoken instructions) through speakers on the wearable device worn by the user. Different tones, frequencies, and volumes can convey various types of feedback. A high-pitched beep might indicate an error, while a low-pitched tone could signify acceptable performance. Spoken instructions can provide specific guidance, such as "reduce force" or "increase precision." If the user's hand tremor exceeds acceptable levels, the system could emit a high-pitched beep or a voice command saying "steady your hand." Visual feedback may also be provided through a display screen, augmented reality (AR) glasses, or LEDs on the wearable device. Visual elements such as color-coded indicators, flashing lights, or on-screen messages, such as message 1540 in FIG. 15E, highlight performance metrics and deviations. Real-time graphs or charts can show trends and variations in the user's performance metrics, offering a comprehensive view. During a procedure, if the user's precision falls below the benchmark, the display might show a red indicator or a flashing message "increase precision."

Figure 5B:
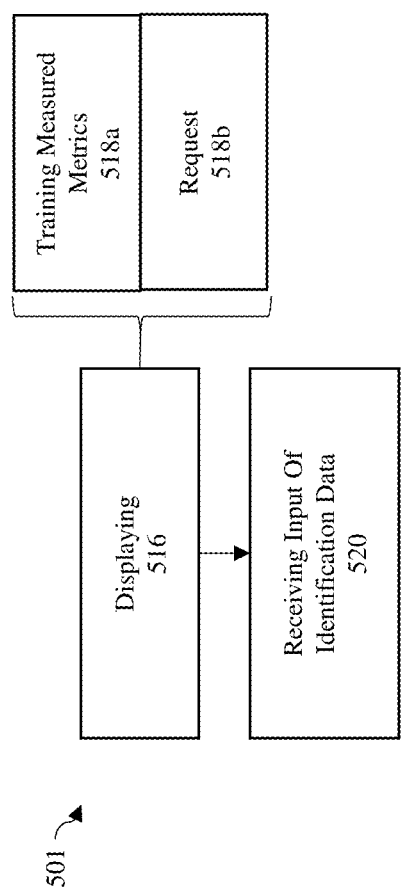
FIG. 5B is a flowchart diagram illustrating steps for a method for requesting identification data, according to an example embodiment.
Figure 12:
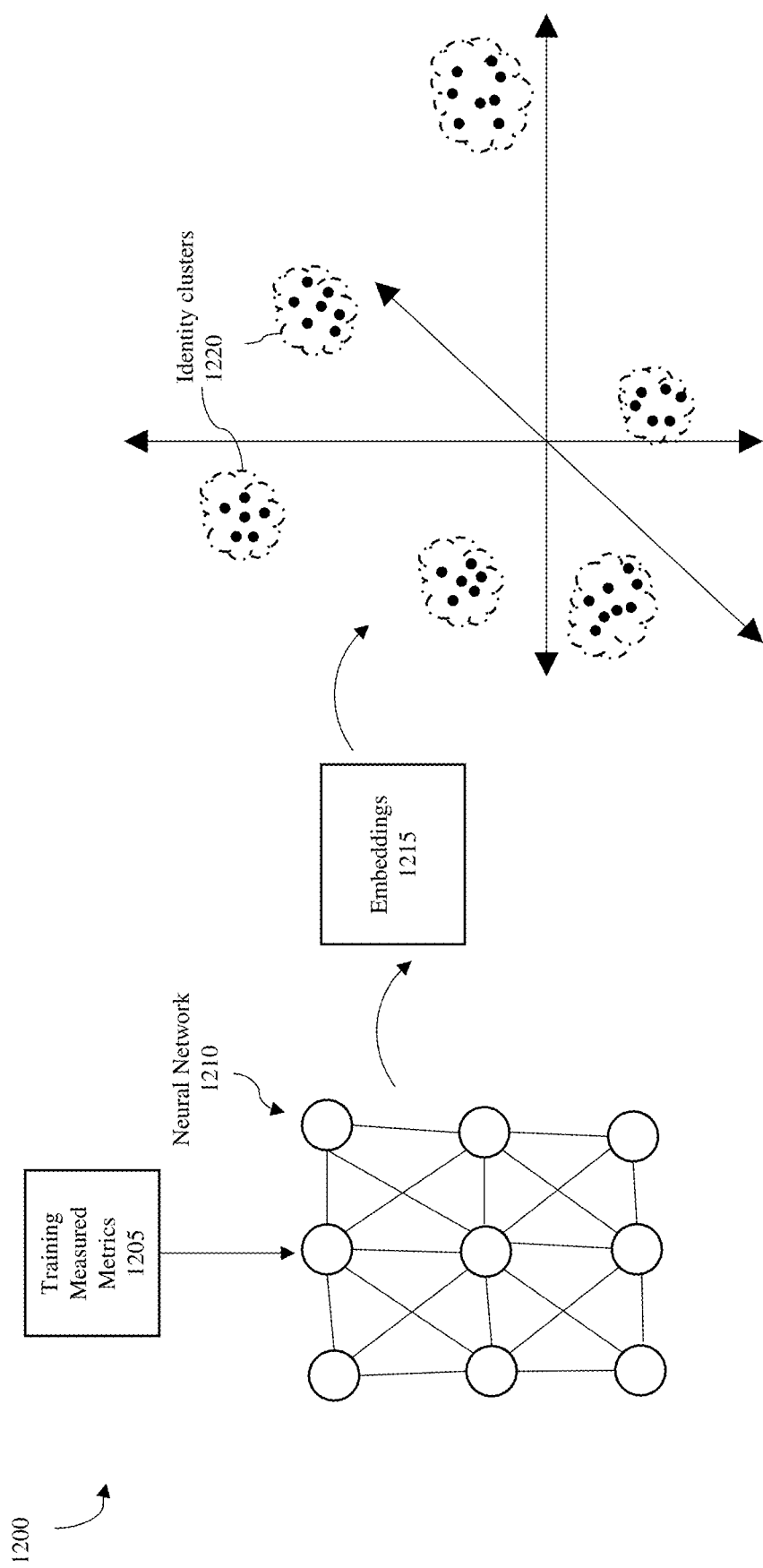
FIG. 12 is a diagram that illustrates certain portions of a process flow for identifying entity clusters from the training measured metrics, according to an example embodiment.
Figure 13:
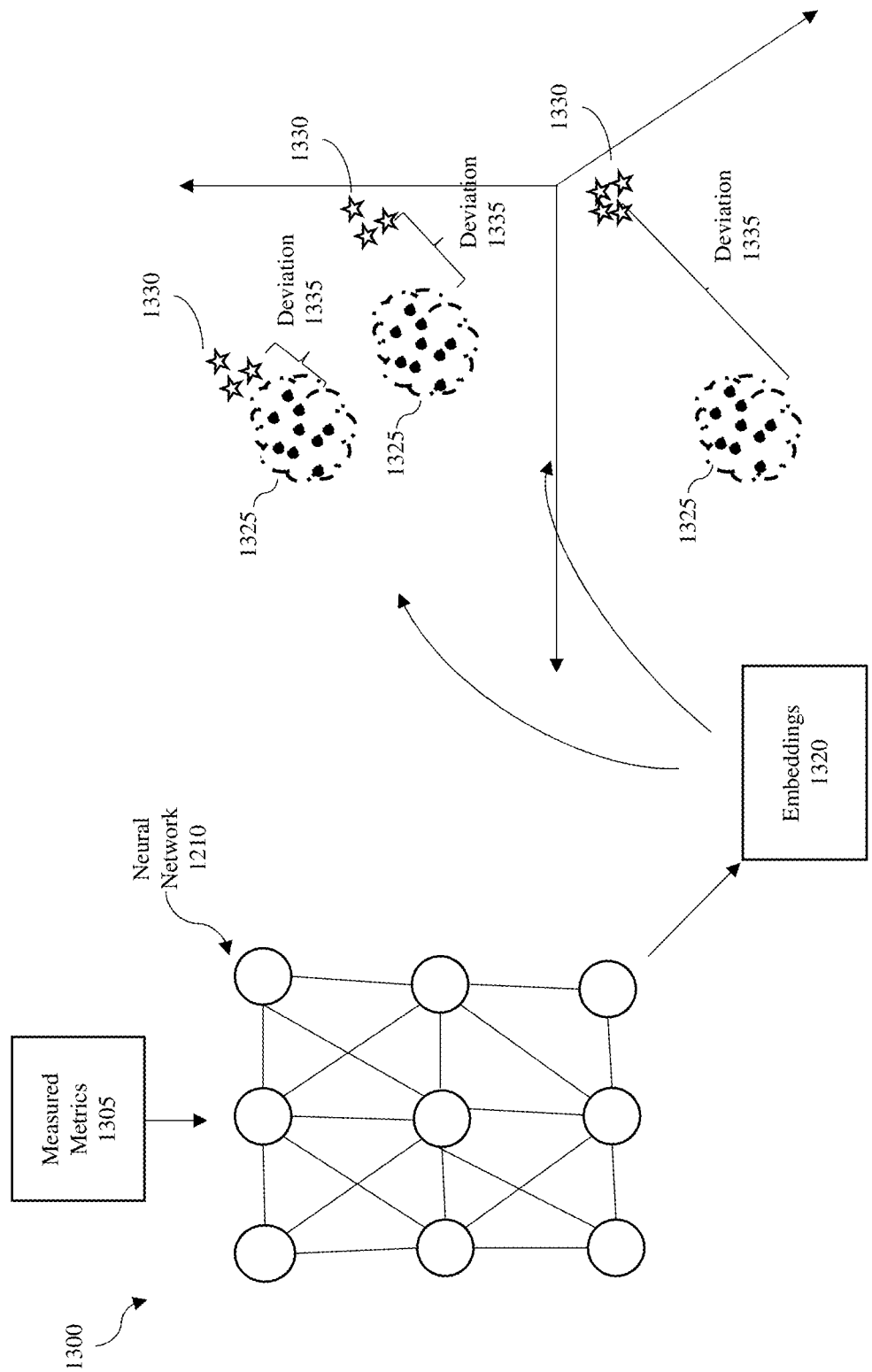
FIG. 13 is a diagram illustrating certain portions of the process flow for identifying entity clusters from the measured metrics, according to an example embodiment.

Referring now to FIGS. 5B, 12, and 13, in some embodiments, method 500 may include process 501, which allows the user to input identification data for the training measured metrics. FIG. 5B is a flowchart diagram illustrating steps for a method for requesting identification data, according to an example embodiment. FIG. 12 is a diagram 1200 that illustrates certain portions of a process flow for identifying entity clusters from the training measured metrics, according to an example embodiment. FIG. 13 is a diagram 1300 illustrating certain portions of the process flow for identifying entity clusters from the measured metrics, according to an example embodiment.

In step 516, method 500 includes displaying, on a display of the remote computing device, the training measured metrics 518a and a request 518b for an input of identification data. The server sends data packet 202, including graphical user interface data and a request for an input of identification data, to network 106. The graphical user interface data is configured to display the training measured metrics and a graphical indicator requesting the second user 120 to input identification data. The user computer device 114 or second user computing device 122 receives data packet 210 including the graphical user interface data and the request.

Figure 9:
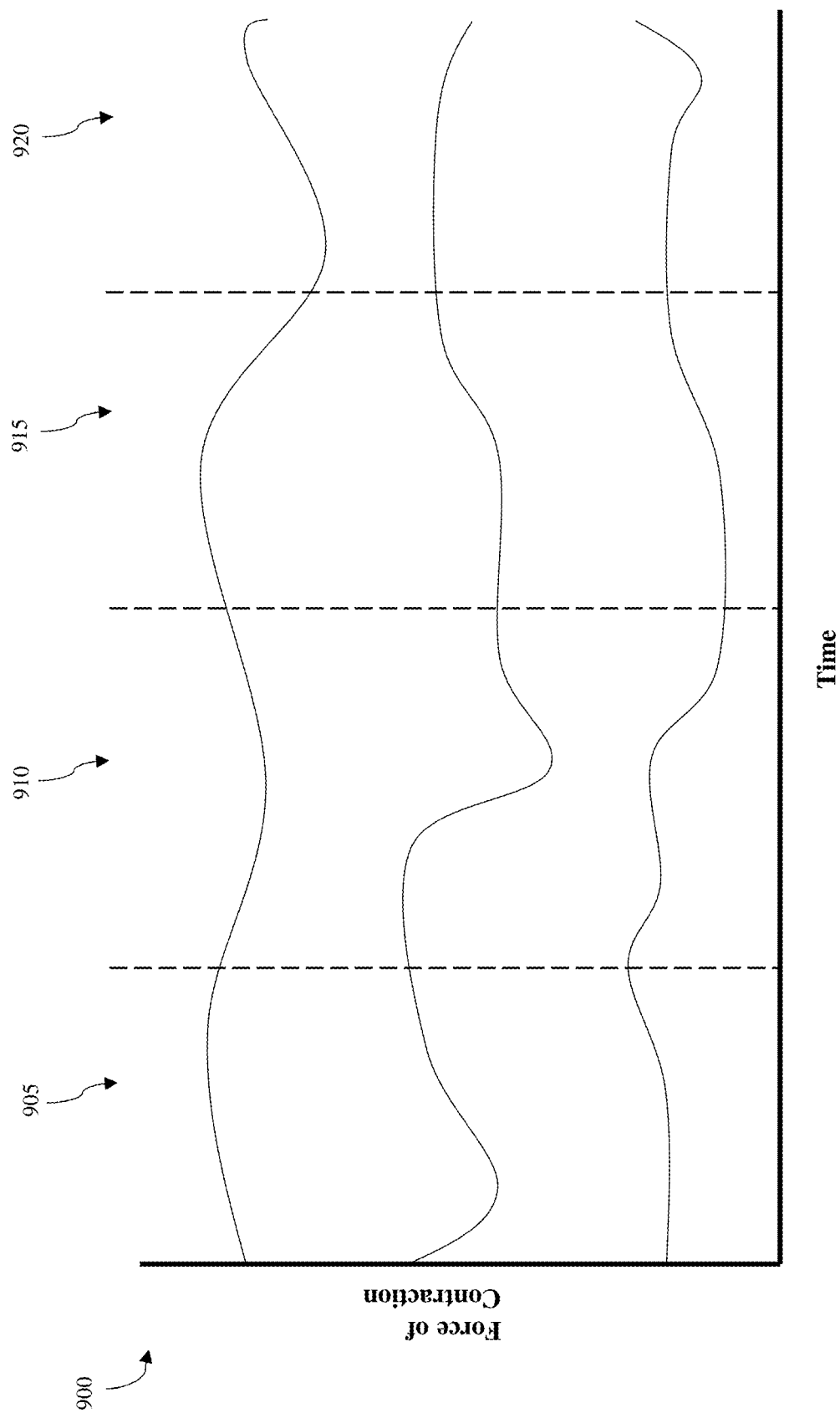
FIG. 9 is a graph illustrating the signals received by the sensors over time, according to an example embodiment.
Figure 10B:
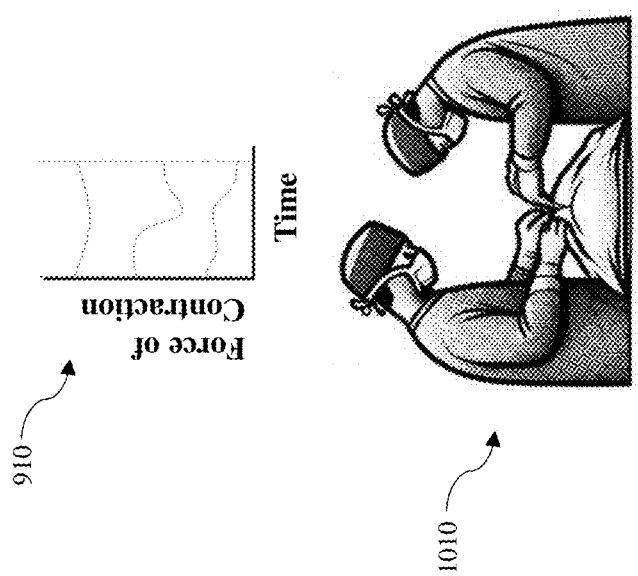
FIG. 10B illustrates a graph corresponding to a procedural segment, according to an example embodiment.
Figure 10A:
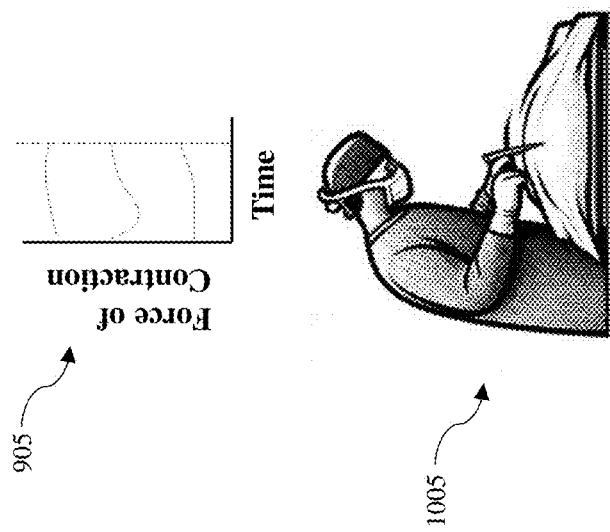
FIG. 10A illustrates a graph corresponding to a procedural segment, according to an example embodiment.
Figure 10D:
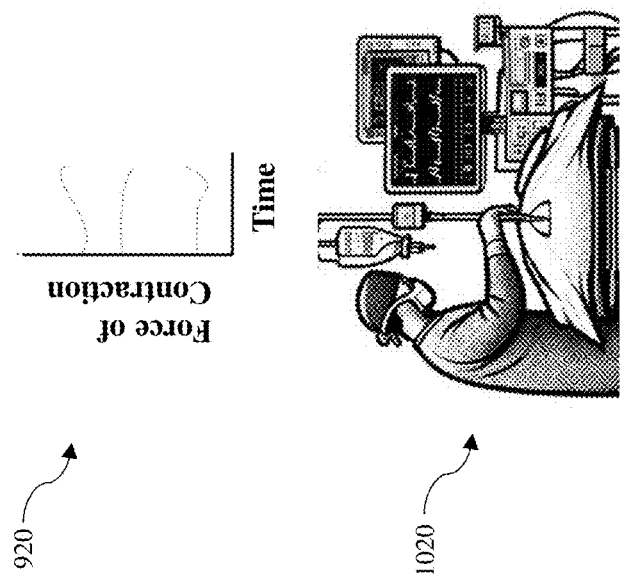
FIG. 10D illustrates a graph corresponding to a procedural segment, according to an example embodiment.
Figure 10C:
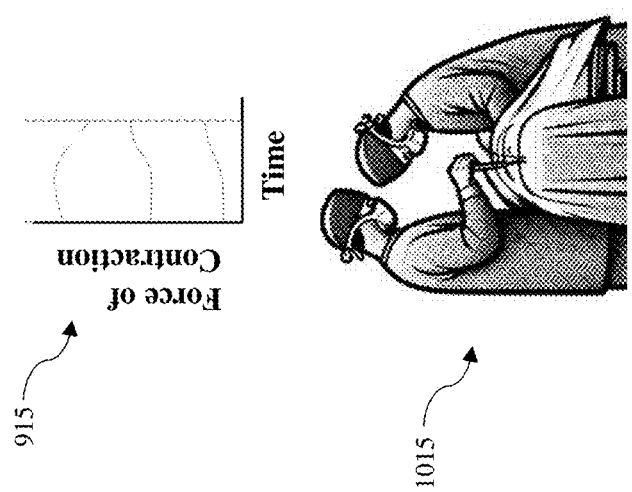
FIG. 10C illustrates a graph corresponding to a procedural segment, according to an example embodiment.

Once displayed on the second user computing device, the graphical user interface includes the data in a user-friendly format. This includes graphical representations such as charts, graphs, and tables to make the data easily interpretable. Graphs and charts allow the second user to visualize metrics like heart rate, muscle activity, movement patterns, and force exertion over time. Tables display numerical values and summaries of the collected metrics. For example, the training measured metrics and measured metrics may include data of force of contractions over time. As shown in FIG. 9, the graph 900 displays said data. The second user may identify segments 905 within the graph that represent different steps during a medical procedure. Those segments 905, 910, 915, and 920 are then divided to correspond with the identified steps 1005, 1010, 1015, and 1020, respectively. This is illustrated in FIGS. 10A through 10D, in which a graphical representation of a procedural segment is associated with a segment of a graph similar to graph 900.

In another example, the training measured metrics and measured metrics may also include location data along with signal data of force exertions of muscles, displayed in table chart 1100 of FIG. 11. Table chart 1100 includes a list of example gestures that occur during a medical procedure along with associated data that defines those gestures. The data for each gesture is measured based on the spatial reference point defined by the calibration of the wearable device. This calibration is further described below with reference to FIG. 7. The training model is configured to identify procedural segments and gestures based on these metrics.

In one example embodiment, shown in FIG. 15B, graphical user interface 1501 for training the neural network is illustrated, according to an example embodiment. Interface 1501 displays the training measure metrics 1510 and a prompt 1512 requesting input 1514 to identify which procedural segment corresponds to the training measured metrics. Interface 1501 may further display a button 1516 to proceed to the next segment.

In some embodiments, during the medical procedure, the system may continuously display metrics in a table format. Once the user or second user notices a procedural segment has ended, they can input identification data for the currently displayed metrics before the next procedural segment begins. The user then inputs identification data by interacting with the graphical user interface on the display of the second user computing device 122. The input of identification data includes at least one of an identification of a type of medical procedure corresponding to the plurality of training measured metrics, an identification of a plurality of procedural segments for the type of medical procedure, and a value for at least one of each procedural segment and the type of medical procedure. Each procedural segment corresponds to a subset of training measured metrics of the plurality of training measured metrics. The value establishes a performance benchmark for each procedural segment.

The term value refers to a specific, quantifiable measure used to establish a performance benchmark for each procedural segment during a medical procedure. This value serves as a critical metric for assessing the quality and effectiveness of the user's actions within a defined segment. Examples of values include the time taken to complete a segment, the force applied, movement precision, muscle activation levels, and physiological responses such as heart rate or oxygen consumption. Additionally, the value could also be a score or ranking that compares the user's performance to a standard or benchmark, which could be derived from the aggregate data of multiple users or established best practices. This score or ranking could be based on the deviation from the benchmark metrics, providing a clear indication of how closely the user's performance aligns with the expected standards. Furthermore, the value could take into account the user's past performances, offering a personalized benchmark that reflects their individual progress and areas for improvement.

For example, during a laparoscopic surgery, the system continuously monitors and displays various metrics related to the user's performance. For example, in the suturing segment, the system measures metrics such as the precision of needle placement, the time taken to complete the suturing, and the force applied. Suppose the benchmark for precision is a deviation of no more than ±1 mm from the ideal path. If the user achieves a deviation of 0.5 mm, the system translates this into a high precision score of 95 out of 100. For the time taken, with a benchmark set at 5 minutes, if the user completes the suturing in 4.8 minutes, they earn a time efficiency score of 90 out of 100 based on the slight deviation from the benchmark. Additionally, the force applied during suturing could be compared to an optimal range, with the user receiving a score or ranking that reflects how well they adhered to the benchmark. These scores are displayed in a table format on the system's graphical user interface, providing immediate feedback and allowing the user or a second user to input identification data that includes these scores. This process ensures that each segment's performance is accurately assessed and benchmarked, facilitating continuous improvement and proficiency in medical procedures.

Next, in step 520, method 500 includes receiving the input of identification data from the remote computing device. After the identification data is input by the second user 120, the second user computing device 122 sends data packet 212 including said identification data to network 106. The server 102 then receives data packet 204, including said identification data, from network 106. Then, based on the identification data for the training measured metrics 1205, the server trains the machine learning model (neural network 1210) to generate, for each type of medical procedure of a plurality of types of medical procedures, a first unique identifier for the type of medical procedure, and at least one second unique identifier for each procedural segment of the plurality of procedural segments of the type of medical procedure. With reference to FIG. 12, the unique identifiers are vector embeddings 1215 that are plotted onto a three-dimensional chart. However, it is understood that the embeddings may be n-dimensional tensors where n is greater than three. These vector embeddings create clusters or identity clusters 1220 that may represent medical procedures or procedural segments. Each cluster is defined by the centroid (average) of the data points within it, representing a typical performance pattern. These identity clusters are used as a basis for future evaluations of medical procedures and segments.

The identification data refers to specific, user-provided information that describes and categorizes the measured metrics associated with different procedural segments of a medical procedure. This identification data includes details such as the type of medical procedure, the specific procedural segments, and performance benchmarks. Once input by the second user, this identification data is sent from the second user computing device to the server via a data packet. The server then uses this data to train the machine learning model, specifically a neural network, to generate unique identifiers for each type of medical procedure and its procedural segments.

The identification data helps train the system to recognize and classify measured metrics accurately as part of specific procedural segments or entire procedures with a high degree of confidence. After the identification data is received from the remote computing device, it is used to label the training measured metrics, thereby providing a clear context for each data point. This labeled data is then fed into the neural network, which is trained to learn the associations between the measured metrics and their corresponding procedural segments or overall procedures.

During the training process, the neural network analyzes the labeled data to identify patterns and relationships within the metrics. It adjusts its internal weights and parameters to minimize the error between its predictions and the actual labels. Through iterative learning and backpropagation, the neural network becomes proficient at distinguishing between different types of procedures and their segments based on the measured metrics.

Once trained, the system can use the neural network to process new sets of measured metrics. When a new data point is input, the neural network generates a vector embedding for it and compares this embedding to the previously learned clusters. By calculating the similarity between the new embedding and the centroids of the clusters, the system determines which cluster the new data point most likely belongs to. This similarity is measured using metrics such as cosine similarity or Euclidean distance.

The degree of confidence in the classification is quantified based on how closely the new data point matches the centroid of the identified cluster. A high degree of similarity indicates a high confidence level that the measured metrics correspond to a specific procedural segment or the entire procedure. This confidence level is crucial for making real-time decisions and providing feedback. For instance, if the confidence level is high, the system can confidently assert that the user is performing a particular step of the procedure correctly. Conversely, lower confidence levels might prompt further verification or additional guidance for the user.

In summary, the identification data trains the system to recognize specific clusters or embeddings as part of particular procedural steps or the entire procedure with a high degree of confidence. This is achieved by learning from labeled training data, identifying patterns, and using similarity measures to classify new data points accurately. This process ensures that the system can provide precise, reliable feedback and predictions during medical procedures.

With reference to FIG. 13, once the server receives measured metrics 1305 during an evaluation, the server analyzes, using the neural network 1210, the measured metrics 1305 collected during the medical procedure with the model to map, using vector embeddings 1320, clusters 1325 defined by the measured metrics. The algorithm identifies natural groupings in the data, where each cluster represents a specific pattern of performance metrics. The server then compares the clusters to the first unique identifiers and the second unique identifiers to predict, with a certain level of confidence, the type of medical procedure being performed by the user and one procedural segment of the procedural segments of the type of medical procedure. The model matches the real-time clusters to the first unique identifiers (procedure types) and second unique identifiers (procedural segments). The model calculates the similarity between the real-time clusters 1325 and the pre-defined identifiers (clusters 1220 from the training measured metrics), determining the likelihood that the current data matches a specific procedure type and segment. The system assigns a confidence score to each prediction based on the degree of similarity. The model predicts the procedure type and segments with the highest confidence scores. The model then identifies outliers 1330 to calculate deviation 1335.

Figure 6:
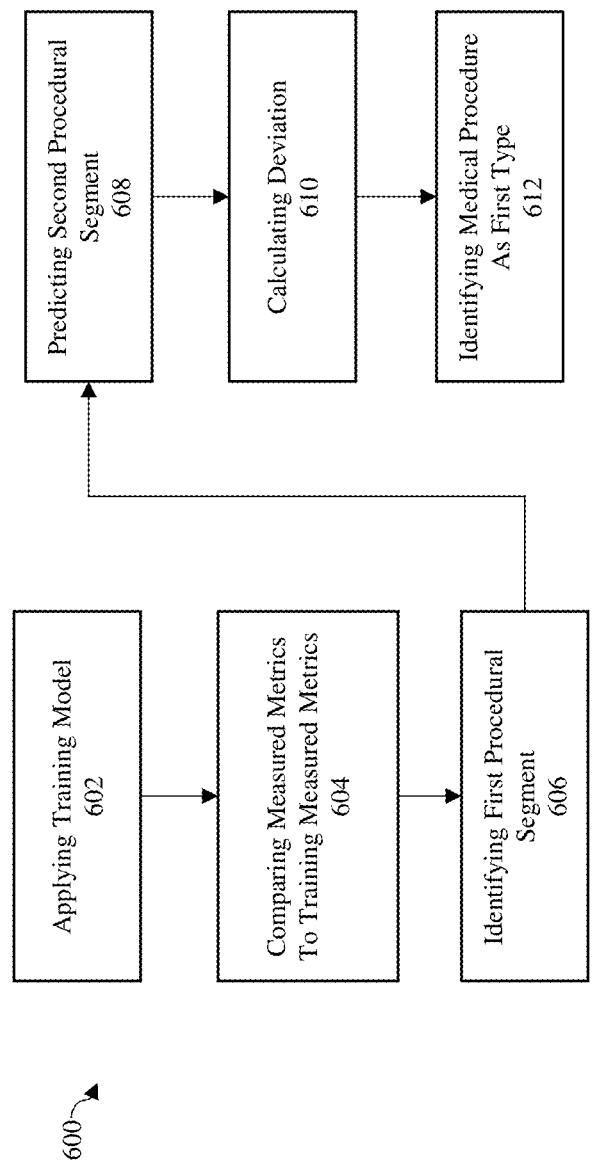
FIG. 6 is a flowchart diagram illustrating steps for a method for evaluating a user's performance of a medical procedure, according to an example embodiment.

Referring now to FIG. 6, a flowchart diagram illustrating steps for a method 600 for analyzing the plurality of measured metrics collected during the medical procedure is shown, according to an example embodiment. In step 602, method 600 includes applying the training model. Each of the plurality of procedural segments for each of the plurality of types of training medical procedures comprises a sub-benchmark of performance. The application of the training model is an interactive and continuous process. As the user performs the procedure, the model continuously monitors and evaluates their performance. The feedback loop helps the user make real-time adjustments to their technique, leading to immediate improvements and skill development. The training model, incorporating machine learning algorithms and neural networks, learns to recognize patterns within procedural segments. It identifies key characteristics and metrics that define each segment.

Next, in step 604, method 600 includes comparing the plurality of measured metrics to the plurality of training measured metrics. The real-time measured metrics are continuously compared to the patterns and metrics associated with each procedural segment in the training model. The model analyzes the incoming data to detect similarities and match it to the most likely segment.

Next, in step 606, method 600 further includes identifying a first procedural segment for the medical procedure by comparing the plurality of measured metrics to the plurality of procedural segments of the training model. The process entails real-time monitoring and comparison of the user's physiological and biomechanical metrics with a trained model's procedural segments. The goal is to correctly identify which segment of the procedure the user is currently performing, based on patterns learned during the training phase. Using algorithms such as dynamic time warping (DTW) or sequence alignment, the model identifies the first procedural segment that the user is currently performing. This involves matching the real-time metrics to the closest corresponding segment from the training data. The model uses predefined thresholds and criteria to determine a match. For instance, specific ranges of heart rate, movement speed, and muscle activity that correspond to the preparation segment. The model calculates confidence levels for each potential segment match. The segment with the highest confidence level, based on the similarity of patterns and metrics, is identified as the current procedural segment. The identified segment is used to provide real-time feedback and guidance to the user. As the procedure progresses, the system continuously monitors and updates the segment identification, ensuring accurate tracking and assessment throughout the entire procedure. This step ensures that each step is accurately recognized and evaluated, facilitating immediate feedback and correction, which is essential for skill development and procedural proficiency.

Next, in step 608, method 600 further includes predicting a second procedural segment for the medical procedure based on the training model. The trained model has learned the typical sequence and characteristics of procedural segments, to forecast the next segment the user is likely to perform. This prediction is based on real-time data and the model's understanding of the procedural workflow. During the training phase, the model learns the typical sequence of procedural segments for each type of medical procedure. This involves understanding the transition patterns and the conditions that trigger the next segment. The model recognizes the patterns and metrics associated with transitions from one segment to the next. It uses these patterns to predict subsequent segments based on the current metrics and procedural context. The model analyzes the current segment's metrics and uses the learned sequential patterns to predict the next segment. For instance, if the current segment is "incision," the model anticipates that the next segment could be "dissection" based on typical procedural flow. The model also considers contextual factors such as the duration of the current segment, user performance, and physiological responses to make an accurate prediction. The model calculates the probabilities of potential next segments using algorithms like Hidden Markov Models (HMMs) or Recurrent Neural Networks (RNNs). These probabilities are based on historical data and the current procedural context. Each potential next segment is assigned a confidence level, indicating the likelihood of it being the correct next step. The segment with the highest confidence level is selected as the predicted next segment.

Step 608 is depicted in FIG. 15C, which is a graphical user interface 1502 that illustrates the prediction of the second procedural segment, according to an example embodiment. Interface 1502 illustrates measured metrics 1518 for the second procedural segment. Interface 1502 displays a prompt 1520 asking if the current segment is the predicted segment. Interface 1501 may further display button 1516 to proceed to the next segment. The user must interact with buttons 1522 or 1524 to confirm whether the system's prediction is correct or not to strengthen the neural network.

Next, in step 610, method 600 further includes calculating the deviation between the sub-benchmark of performance for the second procedural segment predicted by the training model and the plurality of measured metrics collected during the medical procedure. Sub-benchmarks of performance are specific, measurable criteria set for each segment of a medical procedure. Sub-benchmarks are established by analyzing a large dataset of training metrics collected from multiple users performing the same procedures. This data includes physiological and biomechanical parameters relevant to each segment. For each segment, key performance metrics are identified, such as time taken, precision of movements, force exerted, and physiological responses (e.g., heart rate, muscle activity). These metrics are used to define the sub-benchmarks. The real-time measured metrics for the predicted segment are matched with the corresponding sub-benchmarks. Each metric is evaluated individually. The deviation for each metric is calculated by comparing the real-time data to the sub-benchmarks. This involves determining the difference or percentage deviation. In some embodiments, the deviations for all metrics are aggregated to provide an overall performance assessment for the procedural segment. This can be a simple sum, an average, or a weighted sum based on the importance of each metric.

Next, in step 612, method 600 further includes identifying the medical procedure as a first type of one of the plurality of types if the deviation is within a predetermined threshold. This process entails analyzing the real-time metrics collected during a medical procedure, comparing them to established benchmarks for different types of procedures, and using the degree of deviation to identify and confirm the type of procedure being performed. A threshold is established to define the acceptable range of deviation for each metric. This threshold represents the maximum allowable difference between the real-time performance and the benchmark for accurate identification. For example, if the benchmark for heart rate during a procedure is 70 BPM with a threshold of ±10 BPM, any heart rate between 60 BPM and 80 BPM is acceptable. The system aggregates the deviations across all relevant metrics for each procedure type to determine an overall deviation score. The aggregated deviation score is compared against the predetermined threshold for each procedure type. If the deviations for all metrics fall within the acceptable range, the procedure is identified as that specific type. If the deviations are within the threshold for a particular procedure type, the system confirms the identification of the procedure as that type. The system provides feedback based on the identified procedure type, helping the user understand their performance in the context of that specific procedure.

After step 612, the system may send graphical user interface data configured to display graphical user interface 1505 shown in FIG. 15F. Interface 1505 illustrates the type of procedure 1544 along with the next segment 1546 predicted by the trained algorithm. Similarly to interface 1502 in FIG. 15C, interface 1505 displays buttons 1522 and 1524 configured to allow the user to confirm or modify the predicted procedure type and segment.

Figure 7:
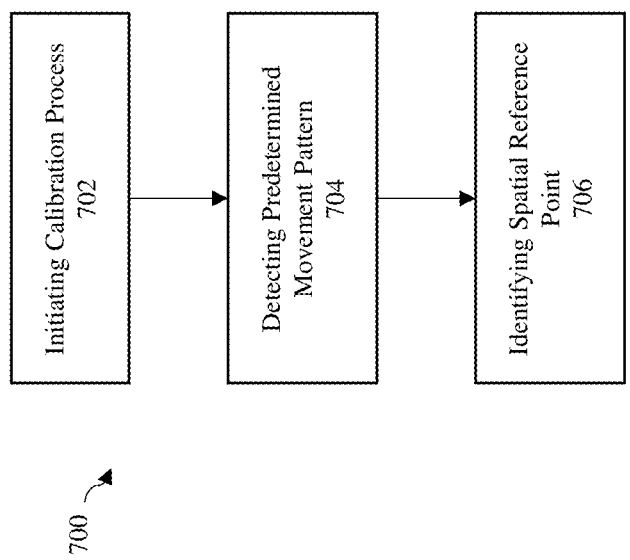
FIG. 7 is a flowchart diagram illustrating steps for a method of a calibration process for the sensor prior to commencing the medical procedure, according to an example embodiment.

Referring now to FIG. 7, a flowchart diagram illustrating steps for a method 700 for evaluating a user's performance of a medical procedure is shown, according to an example embodiment. In step 702, method 700 includes initiating a calibration process for the sensor prior to commencing the medical procedure. The calibration process is a preparatory step that adjusts the sensor to account for individual variations in physiological and biomechanical metrics. This ensures the data collected during the medical procedure is accurate. The user verifies that the wearable device is properly placed to ensure optimal sensor contact with the skin.

Next, in step 704, method 700 includes detecting a predetermined movement pattern corresponding to a gesture to initiate the collecting of a plurality of sensor data. A predetermined movement pattern refers to a specific, deliberate sequence of physical motions that the system recognizes as a trigger to initiate the collection of sensor data. This pattern is designed to be easily identifiable and consistently reproducible, ensuring that the calibration process is accurate and reliable. Examples of such patterns might include a series of wrist rotations, opening and closing the hand multiple times, flexing and extending the arm in a specific manner, or performing a set sequence of finger movements. These metrics are then stored in a database so that they are predetermined for the user to perform and the system to recognize, providing a reference framework that ensures the sensor is correctly calibrated to the user's specific movements and physiological responses. This stored data is crucial for accurately initiating and interpreting subsequent sensor data collection during the actual procedure. This calibration step uses a deliberate and recognizable movement pattern as a trigger to start the sensor's data collection process. The predefined gesture ensures that the sensor is correctly calibrated to the user's specific movements and physiological responses.

Next, in step 706, method 700 further includes identifying at least one spatial reference point. The sensor collects a position of the sensor relative to the spatial reference point and a state of a plurality of muscles of the user performing the medical procedure. The state of a plurality of muscles, or muscle state, encompasses various aspects of muscle activity, including contraction levels, fatigue, coordination, strength, tone, and physiological parameters. Muscle activation is measured by electromyography (EMG) sensors, which detect the electrical activity generated by the firing of action potentials during muscle contractions. This electrical activity generates currents that provide detailed information about muscle contraction levels and patterns. Muscle fatigue is assessed through endurance and recovery rates, with indicators such as a decrease in muscle force output and changes in EMG signal amplitude and frequency. Coordination is evaluated by examining the synergistic and antagonistic actions of muscles, ensuring smooth and precise movements. Muscle strength and force are measured using force sensors and dynamometers, which capture the force output and maximum strength levels of muscles. Muscle tone, both resting and dynamic, is monitored to understand the baseline tension and changes during activity. Physiological parameters, such as oxygen consumption and blood flow, are measured using techniques like near-infrared spectroscopy (NIRS), providing insights into metabolic efficiency and vascular health. Additionally, motion capture systems track the velocity and acceleration of movements, offering data on the coordination and performance of muscle groups. By integrating these measurements, the system continuously monitors the state of muscles, allowing for real-time assessment and feedback. This comprehensive monitoring is crucial for applications in medical procedures, athletic training, and rehabilitation, where understanding muscle state can lead to improved performance and outcomes. During the medical procedure, the wearable device monitors the state of the muscles which is assessed through the various measured metrics that provide a real-time understanding of muscle function and performance.

This step involves the system recognizing and using specific, predefined locations in the environment as reference points. These points help calibrate the sensor's spatial awareness, enabling more accurate tracking of movements and positioning. The system uses the known positions of the reference points to establish a coordinate system. This allows the system to accurately determine the user's position and movements relative to these points. For example, the sensor calculates distances and angles between the user's movements and the reference points.

The system identifies at least one spatial reference point using data from wearable devices and environmental sensors. The wearable devices, equipped with sensors such as accelerometers, gyroscopes, and magnetometers, collect real-time data on the user's movements. The environment may also contain fixed sensors or markers, such as RFID tags, infrared markers, or visual markers, to provide additional spatial references. During the initial calibration, the user performs specific gestures, allowing the system to establish a baseline and reference framework. The spatial reference points can be defined in various embodiments. In one embodiment, the spatial reference is relative to the user, where the origin (0,0,0) of the spatial grid is set at a specific point on the wearable device, such as the wrist. This allows the system to track the user's movements accurately relative to their body. In another embodiment, the spatial reference is relative to the room or the environment, using fixed markers or sensors to establish a global reference frame. Here, the origin might be a designated point in the room, providing a consistent external frame of reference. These spatial references are crucial for accurately tracking and analyzing the user's movements, ensuring precise alignment of procedural segments and performance metrics.

The system establishes the spatial grid through a comprehensive process that involves sensor integration, calibration, and algorithmic processing. Initially, the user wears devices equipped with sensors such as accelerometers, gyroscopes, magnetometers, and possibly cameras or optical sensors. The environment may also contain fixed sensors or markers, such as RFID tags, infrared markers, or visual markers, to provide additional spatial references. During the initial calibration phase, the user performs specific predefined movements or gestures, allowing the system to collect baseline sensor data and establish the initial orientation and position of the wearable devices relative to both the user and the environment.

The system then fuses data from the various sensors, integrating information on movement, rotation, and orientation to create a cohesive understanding of the spatial environment. It identifies fixed reference points from the environmental sensors or markers to enhance accuracy. The origin point (0,0,0) of the spatial grid is defined based on the chosen embodiment: it can be user-centric, with the origin set on the wearable device (such as the wrist), or environment-centric, with the origin set at a designated point in the room or surgical field.

Using data from the calibration movements and fixed reference points, the system aligns the spatial grid, calculating the relative positions and orientations. It continuously updates the grid in real-time based on ongoing sensor data, ensuring accurate tracking and alignment. Verification movements may be performed to confirm the grid's accuracy, and any discrepancies are fine-tuned through a feedback loop. This dynamic and precise spatial grid establishment allows for reliable analysis of the user's performance during medical procedures.

Figure 8:
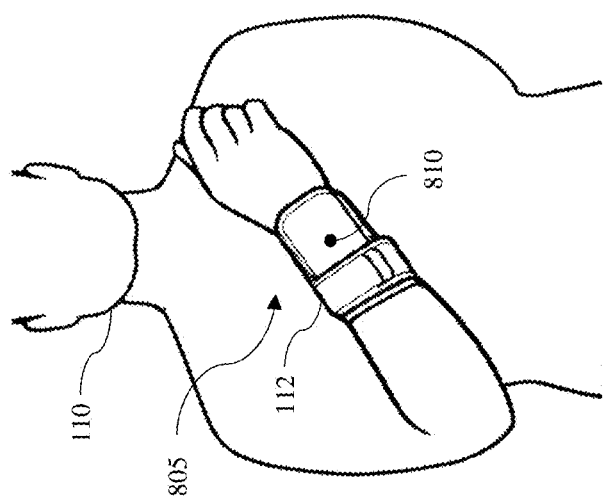
FIG. 8 is a diagram of the user in a calibration position, according to an example embodiment.

In one embodiment, as shown in FIG. 8, the calibration process includes the user 110 placing the wearable device 112 directly on their chest area 805 to set a spatial reference point 810. For location related data of the measured metrics, the system uses a special reference point at the chest to measure where the user's arm or hand is moving.

Referring now to FIG. 12, a diagram illustrating an embodiment for components of processing a plurality of training measured metrics to generate an authentic neural network, according to an example embodiment. The training measured metrics 1205 are processed by the neural network 1210 using the processor of the server 102 of the system that may be stored in the connected database 104 of the system. Due to the neural network processing, the neural network can be used as a predictive tool. In one embodiment, given a supposed medical procedure and its segments from a second user and at least some training measured metrics associated with the medical procedure and its segments, the processor using the neural network can make predictions about possible unknown metrics associated with the message provided by the candidate entity. In this regard, neural networks that may be useful may include perceptron, feed forward, radial basis network, deep feed forward, recurrent neural network, long/short term memory, gated recurrent unit, auto encoder, variational auto encoder, denoising autoencoder, sparse autoencoder, Markov chain, Hopfield network, Boltzmann machine, restricted Boltzmann machine, deep belief network, deep convolutional network, deconvolutional network, deep convolutional inverse graphics network, deep residual network, Kohonen Network, Support Vector Machine, and Neural Turing Machine, among others. However, other types of neural networks may be used and are within the spirit and scope of the present invention.

As noted above, the systems and methods described herein may also be useful in other digital programmatic systems. Thus, other digital programmatic systems may similarly utilize the receiving training measured metrics, conducting experiments on training metrics, and generating an authentic neural network steps to the same effect, i.e., a trained neural network that may be used to establish the medical procedures, known training measured metrics of the identities, to which the real-time measured metrics will be compared to.

Figure 14:
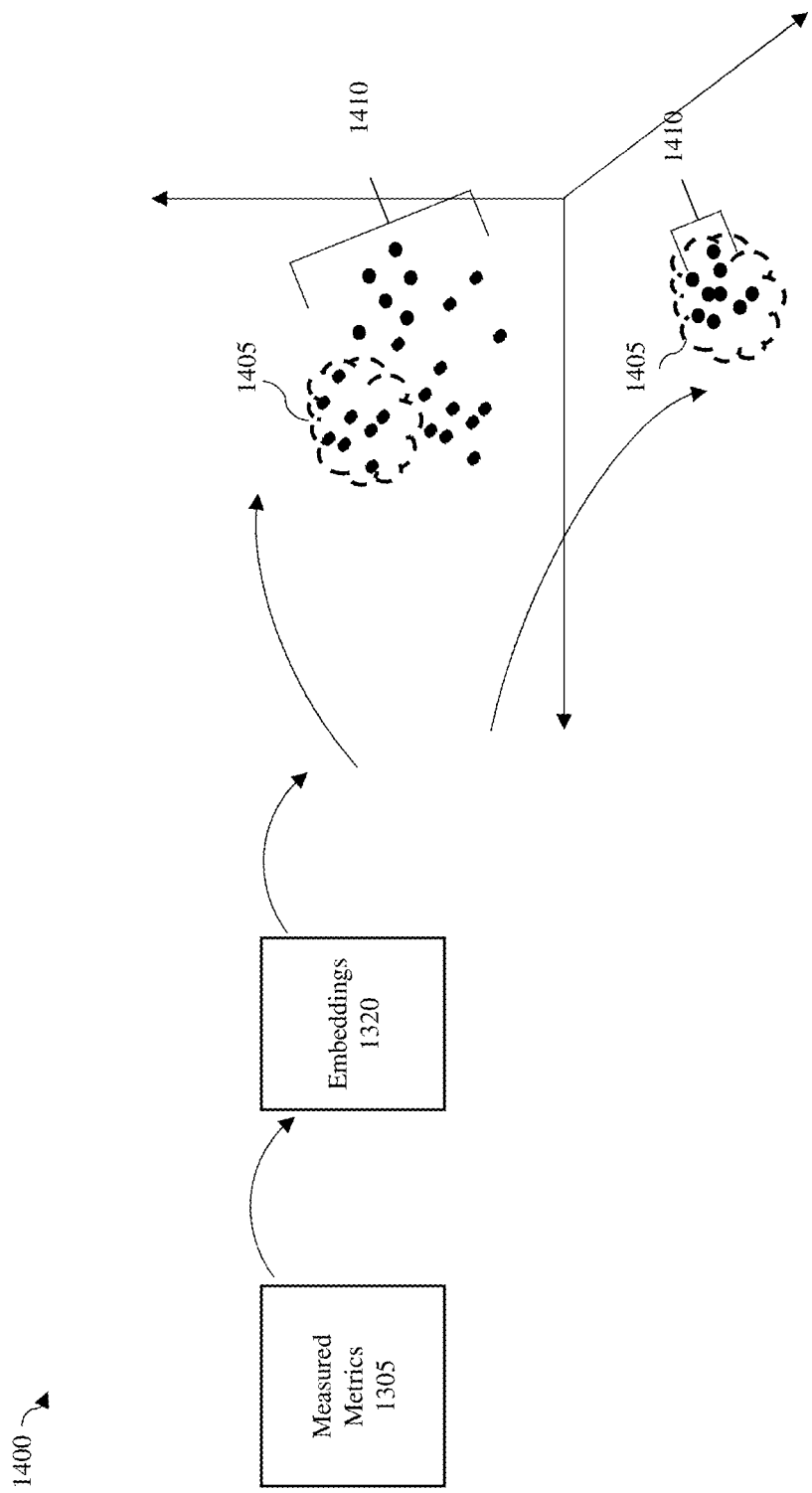
FIG. 14 is a process flow of an embodiment of a method for computing a more complete identity cluster, according to an example embodiment.

Referring now to FIG. 14 where a plurality of measured metrics embeddings 1410 are plotted or positioned outside of the known medical procedure cluster 1405, the server may be determining an output having an indication with a low level of confidence that the medical procedure cluster is a known entity. FIG. 14 is a process flow 1400 of an embodiment of a method for computing a more complete identity cluster 1405, according to an example embodiment; When the plurality of measured metrics embeddings 1410 are plotted inside of the known entity cluster 1405, the server may be determining an output having an indication with a high level of confidence that the measured metrics identity is a known entity. The clustering algorithms will determine within a certain degree of tolerance, certainty, or confidence whether the measured metrics identity is a certain medical procedure or segment. In certain instances, depending on the confidence level after measured metric are received, the system will send feedback data to the first user or second user. The measured metrics embeddings and the identity cluster will be combined using the machine learning clustering algorithms to update the neural network and improve its predictive accuracy. This updated identity will be compared to future identities within the neural network to determine a level of confidence that measured metrics correspond to the correct medical procedures and segments.

With reference to FIG. 15A, a webpage 1500 including a procedure type and its procedural segments is illustrated, according to an example embodiment. The webpage is configured to be displayed on the user computing device and/or second user computing device. Webpage 1500 displays the name or type of procedure 1595 being performed and analyzed. The webpage further displays the list of steps or procedural segments 1596 corresponding to the type of procedure. Underneath the list of steps, a button 1597 for indicating the start of the procedure is displayed. This button causes the system to start collecting metrics from the wearable device worn by the user performing the procedure. The webpage may also include the name 1598 of the user or second user accessing the webpage.

Figure 16:
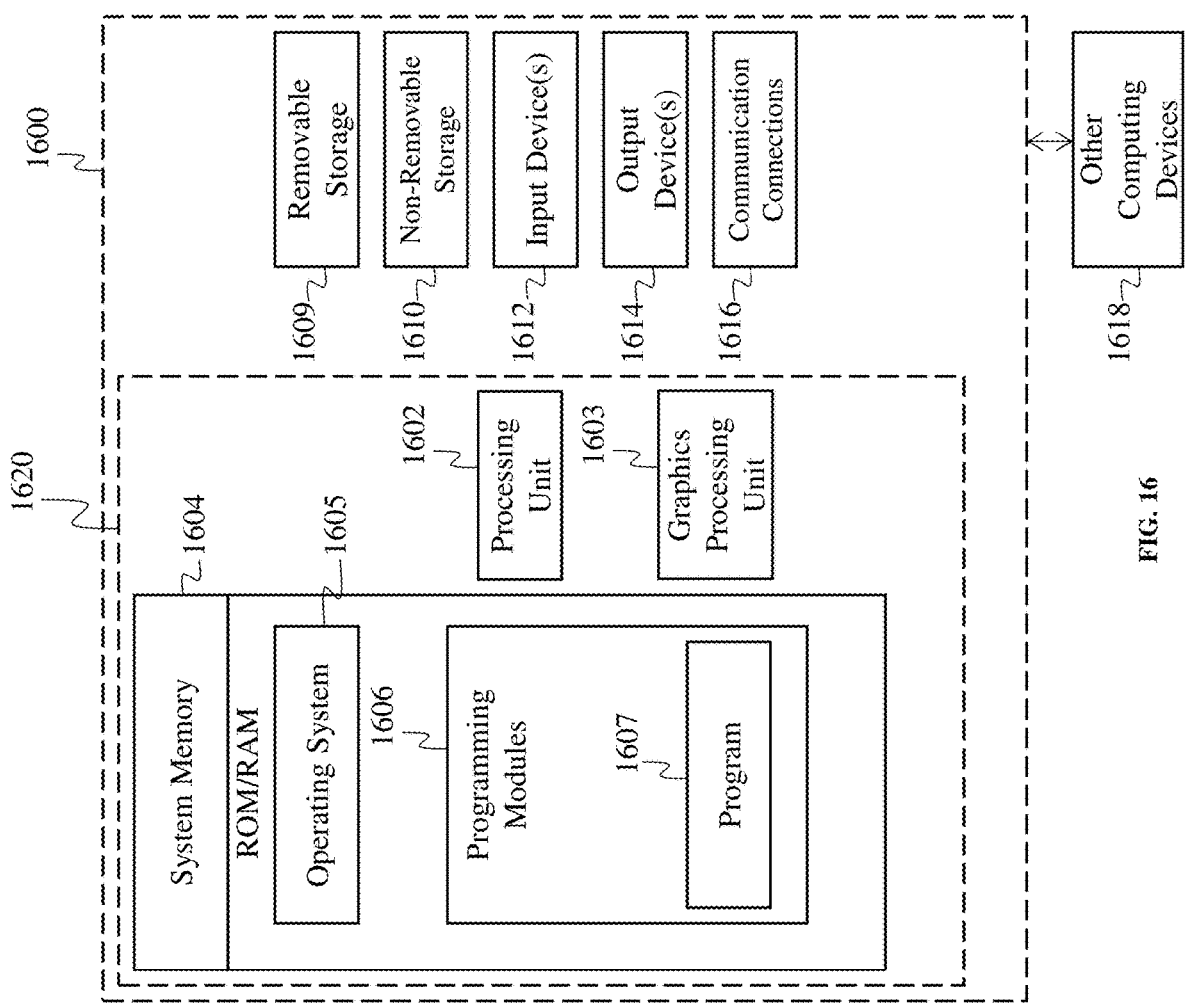
FIG. 16 is a block diagram of a system including an example computing device and other computing devices, according to an example embodiment.

FIG. 16 is a block diagram of a system including an example computing device 1600 and other computing devices. Consistent with the embodiments described herein, the aforementioned actions performed by server 102 or computing devices 112, 114, and 122 may be implemented in a computing device, such as the computing device 1600 of FIG. 16. Any suitable combination of hardware, software, or firmware may be used to implement the computing device 1600. The aforementioned system, device, and processors are examples and other systems, devices, and processors may comprise the aforementioned computing device. Further-more, computing device 1600 may comprise an operating environment for the methods shown in FIGS. 5 through 7 above.

With reference to FIG. 16, a system consistent with an embodiment of the invention may include a plurality of computing devices, such as computing device 1600. In a basic configuration, computing device 1600 may include at least one processing unit 1602 and a system memory 1604. Depending on the configuration and type of computing device, system memory 1604 may comprise, but is not limited to, volatile (e.g., random access memory (RAM)), nonvolatile (e.g., read-only memory (ROM)), flash memory, or any combination or memory. System memory 1604 may include operating system 1605, one or more programming modules 1606 (such as program module 1607). Operating system 1605, for example, may be suitable for controlling computing device 1600's operation. In one embodiment, programming modules 1606 may include, for example, a program module 1607. Furthermore, embodiments of the invention may be practiced in conjunction with a graphics library, other operating systems, or any other application program and is not limited to any particular application or system. This basic configuration is illustrated in FIG. 1600 by those components within a dashed line 1620.

Computing device 1600 may have additional features or functionality. For example, computing device 1600 may also include additional data storage devices (removable and/or non-removable) such as, for example, magnetic disks, optical disks, or tape. Such additional storage is illustrated in FIG. 16 by a removable storage 1609 and a non-removable storage 1610. Computer storage media may include volatile and nonvolatile, removable, and non-removable media implemented in any method or technology for storage of information, such as computer readable instructions, data structures, program modules, or other data. System memory 1604, removable storage 1609, and non-removable storage 1610 are all computer storage media examples (i.e., memory storage.) Computer storage media may include, but is not limited to, RAM, ROM, electrically erasable read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store information, and which can be accessed by computing device 1600. Any such computer storage media may be part of device 1600. Computing device 1600 may also have input device(s) 1612 such as a keyboard, a mouse, a pen, a sound input device, a camera, a touch input device, etc. Output device(s) 1614 such as a display, speakers, a printer, etc. may also be included. The aforementioned devices are only examples, and other devices may be added or substituted.

Computing device 1600 may also contain a communication connection 1616 that may allow device 1600 to communicate with other computing devices 1618, such as over a network in a distributed computing environment, for example, an intranet or the Internet. Communication connection 1616 is one example of communication media.

Communication media may typically be embodied by computer readable instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, and not limitation, communication media may include wired media such as a wired network or direct-wired connection, and wireless media such as acoustic, radio frequency (RF), infrared, and other wireless media. The term computer readable media as used herein may include both computer storage media and communication media.

As stated above, a number of program modules and data files may be stored in system memory 1604, including operating system 1605. While executing on processing unit 1602, programming modules 1606 may perform processes including, for example, one or more of the methods shown in FIGS. 5 through 7 above. Computing device 1600 may also include a graphics processing unit 1603, which supplements the processing capabilities of processor 1602 and which may execute programming modules 1606, including all or a portion of those processes and methods shown in FIGS. 5 through 7 above. The aforementioned processes are examples, and processing units 1602, 1603 may perform other processes. Other programming modules that may be used in accordance with embodiments of the present invention may include electronic mail and contacts applications, word processing applications, spreadsheet applications, database applications, slide presentation applications, drawing or computer aided application programs, etc.

Generally, consistent with embodiments of the invention, program modules may include routines, programs, components, data structures, and other types of structures that may perform particular tasks or that may implement particular abstract data types. Moreover, embodiments of the invention may be practiced with other computer system configurations, including handheld devices, multiprocessor systems, microprocessor based or programmable consumer electronics, minicomputers, mainframe computers, and the like. Embodiments of the invention may also be practiced in distributed computing environments where tasks are performed by remote processing devices that are linked through a communications network. In a distributed computing environment, program modules may be located in both local and remote memory storage devices.

Furthermore, embodiments of the invention may be practiced in an electrical circuit comprising discrete electronic elements, packaged or integrated electronic chips containing logic gates, a circuit utilizing a microprocessor, or on a single chip (such as a System on Chip) containing electronic elements or microprocessors. Embodiments of the invention may also be practiced using other technologies capable of performing logical operations such as, for example, AND, OR, and NOT, including but not limited to mechanical, optical, fluidic, and quantum technologies. In addition, embodiments of the invention may be practiced within a general-purpose computer or in any other circuits or systems.

Embodiments of the present invention, for example, are described above with reference to block diagrams and/or operational illustrations of methods, systems, and computer program products according to embodiments of the invention. The functions/acts noted in the blocks may occur out of the order as shown in any flowchart. For example, two blocks shown in succession may in fact be executed substantially concurrently or the blocks may sometimes be executed in the reverse order, depending upon the functionality/acts involved.

While certain embodiments of the invention have been described, other embodiments may exist. Furthermore, although embodiments of the present invention have been described as being associated with data stored in memory and other storage mediums, data can also be stored on or read from other types of computer-readable media, such as secondary storage devices, like hard disks, floppy disks, or a CD-ROM, or other forms of RAM or ROM. Further, the disclosed methods stages may be modified in any manner, including by reordering stages and/or inserting or deleting stages, without departing from the invention.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

The invention claimed is:

1. A method identifying a procedural segment of a plurality of procedural segments of a medical procedure for evaluating a user's performance of the medical procedure, the method comprising:

detecting using an electromyogram (EMG) sensor in a device, worn by the user on the user's wrist, electrical activity data produced by a user's muscle caused by a plurality of contraction states of the muscle detected by the EMG sensor over a period of time while the user performs the medical procedure;

wherein the EMG sensor is disposed on an underside of the device such that the EMG sensor maintains contact with the user's skin; wherein a first EMG sensor is disposed over a first muscle group and a second EMG sensor is disposed over a second muscle group, wherein the first muscle group and the second muscle group are at least one of (i) wrist flexors and wrist extensors, and (ii) finger flexors and finger extensors;

detecting from the accelerometer in the device, worn by the user on the user's wrist, spatial reference data comprising a plurality of spatial reference points for the device detected by the accelerometer over a period of time while the user performs while the user performs the medical procedure;

wherein the electrical activity data and spatial reference data received during the performance of the medical procedure over the period of time define a plurality of measured metrics;

transmitting the plurality of measured metrics to at least one processor;

converting, with the at least one processor, the plurality of measured metrics to at least one first embedding, wherein the at least one first embedding is a vector representation of a relationship between each measured metric of the plurality of measured metrics;

plotting, with the at least one processor, the at least one first embedding to a coordinate system in a multidimensional space;

generating, with the at least one processor, a plurality of identity clusters, wherein each identity cluster of the plurality of identity clusters is a digital identity for at least one procedural segment of the plurality of procedural segments of the medical procedure, and wherein the plurality of clusters defines a second digital identity for the medical procedure;

training a neural network based on the plurality of identity clusters and the plurality of measured metrics represented as the at least one first embedding, wherein the plurality of identity clusters define a plurality of stored identity clusters;

calibrating the device to detect a second plurality of measured metrics of an unidentified procedural segment of an unknown medical procedure, wherein calibrating the device comprises;

moving the device proximate to the chest of the user performing the unidentified medical procedure and, based on a first set of data recorded using the accelerometer in the device, generating a first spatial reference point that is proximate to the chest of the user;

moving the device proximate to a patient that the unknown medical procedure is being performed on, and based on a second set of data recorded using the accelerometer in the device, generating a second spatial reference point that is proximate to the patient;

moving the device to a resting position and based on a third set of data recorded using the accelerometer in the device, generating a third spatial reference point that relative to the resting position;

generating an operational coordinate system that is a spatial reference grid within an operating environment that the unknown medial procedure is being performed within, based on the first spatial reference point, the second spatial reference point, and the third spatial reference point;

detecting, using the EMG and the accelerometer in the device, a second plurality of measured metrics of the unidentified procedural segment and transmitting the second plurality of measured metrics to the at least one processor;

converting, with the at least one processor, the second plurality of measured metrics to at least one second embedding;

mapping, with the at least one processor, the at least one second embedding to the coordinate system;

generating, using a k-means clustering algorithm executable with the at least one processor, at least one second identity cluster;

calculating a degree of confidence as a function of the Euclidean distance between the at least one second identity cluster and at least one stored identity cluster of the plurality of stored identity cluster that the second identity cluster purports to be;

identifying, with the at least one processor, the procedural segment that is the unidentified procedural segment associated with the at least one second identity cluster by calculating a degree of confidence based on a quantified difference between the at least one second identity cluster and at least one stored identity cluster of the plurality of stored identity cluster;

comparing, with the at least one processor, the second plurality of measured metrics associated with the identified procedural segment to predefined performance benchmarks, wherein the predefined performance benchmarks represent optimal performance standards for the identified procedural segment based on a historical dataset associated with the identified procedural segment;

calculating, with the at least one processor, a performance deviation between the second plurality of measured metrics and the predefined performance benchmarks, wherein the performance deviation quantifies a difference in at least one of electrical activity data and spatial reference data over the period of time; and training the neural network on the performance deviation, the at least one second identity cluster, and the second plurality of measured metrics represented by the at least one second embedding.

2. The method of claim 1 further comprising the step of, if the performance deviation is a movement path deviation based on the spatial reference data and the electrical activity data that fails to satisfy a second predefined performance benchmark, then sending a second signal to the device to convey real-time feedback to the user; wherein the real-time feedback is a notification to the user that is defined by at least one of a haptic vibration of the device using a haptic actuator disposed on the device, an auditory instruction using a speaker disposed on the device, and a visual indicator using a light-emitting diode on the device.

* * * * *